US012127854B2

(12) United States Patent
Costantine et al.

(10) Patent No.: US 12,127,854 B2
(45) Date of Patent: Oct. 29, 2024

(54) ANTENNA ARRAY OR A GROUP OF ANTENNA ELEMENTS FOR BIOMARKER MONITORING, NERVE STIMULATIONS AND METHODS OF USE

(71) Applicant: American University of Beirut, Beirut (LB)

(72) Inventors: Joseph Costantine, Albuquerque, NM (US); Rouwaida Kanj, Portland, OR (US); Youssef Tawk, Albuquerque, NM (US); Assaad Eid, Paris (FR); Jessica Hanna, Ferzol (LB); Ali H. Ramadan, Beirut (LB)

(73) Assignee: American University of Beirut, Beirut (LB)

( * ) Notice: Subject to any disclaimer, the term of this patent is extended or adjusted under 35 U.S.C. 154(b) by 730 days.

(21) Appl. No.: 17/387,498

(22) Filed: Jul. 28, 2021

(65) Prior Publication Data

US 2022/0054087 A1     Feb. 24, 2022

Related U.S. Application Data

(60) Provisional application No. 63/057,624, filed on Jul. 28, 2020.

(51) Int. Cl.
*A61B 5/00* (2006.01)
*A61B 5/05* (2021.01)
*A61B 5/145* (2006.01)

(52) U.S. Cl.
CPC ........ *A61B 5/6877* (2013.01); *A61B 5/14532* (2013.01); *A61B 5/14546* (2013.01); *A61B 5/4836* (2013.01); *A61B 5/6828* (2013.01); *A61B 2562/046* (2013.01)

(58) Field of Classification Search
CPC ............ A61B 5/14532; A61B 5/14546; A61B 5/4836; A61B 5/6828; A61B 5/05
See application file for complete search history.

(56) References Cited

U.S. PATENT DOCUMENTS

| | | | |
|---|---|---|---|
| 10,405,794 B2 | 9/2019 | Begtrup et al. | |
| 2014/0163338 A1 | 6/2014 | Roesicke | |
| 2015/0150505 A1 | 6/2015 | Kaskoun et al. | |
| 2016/0072554 A1 | 3/2016 | Sharma et al. | |
| 2017/0303858 A1* | 10/2017 | Barak | A61B 5/02125 |
| 2017/0308813 A1 | 10/2017 | Boyden et al. | |
| 2019/0076033 A1 | 3/2019 | Sweeney et al. | |
| 2019/0388000 A1 | 12/2019 | Costantine et al. | |

FOREIGN PATENT DOCUMENTS

WO     2019076733     4/2019

OTHER PUBLICATIONS

WIPO, International Search Report issued in corresponding application, PCT/US2021/043504 issued Nov. 2, 2021, 2 pages.

(Continued)

*Primary Examiner* — Eric F Winakur
(74) *Attorney, Agent, or Firm* — J. Peter Paredes; Amin Wasserman Gurnani LLP

(57) ABSTRACT

Provided herein are systems, methods and apparatuses an antenna array or a group of antenna elements for biomarker monitoring, nerve stimulations, and methods of use.

19 Claims, 15 Drawing Sheets

(56) References Cited

OTHER PUBLICATIONS

Adafruit, "Flora Accelerometer/Compass Sensor—LSM303—v1. 0." [Online]. Available: https://www.adafruit.com/product/1247, 8 pages [Accessed on Mar. 8, 2022].
Ansys, Inc., "Ansys electronics desktop." 2021, [Online]. Available: https://www.ansys.com/products/electronics, 5 pages. [Accessed on Mar. 1, 2022].
Bondia, J. et al., "Using Support Vector Machines to Detect Therapeutically Incorrect Measurements by the MiniMed CGMS®," J. Diabetes Sci. Technol., vol. 2, No. 4, pp. 622-629, 2008.
Bruen, D. et al., "Glucose Sensing for Diabetes Monitoring: Recent Developments," Sensors, vol. 17, No. 8, p. 1866, 2017, (21 pages).
Burge, M. R. et al., "Continuous Glucose Monitoring: The Future of Diabetes Management," Diabetes Spectr., vol. 21, No. 2, pp. 112-119, 2008.
Chen, Z. et al., "Stretchable conductive elastomer for wireless wearable communication applications," Scientific Reports, 7: 10958, 2017, 8 pages.
Choi, H., "Recent Developments in Minimally and Truly Non-Invasive Blood Glucose Monitoring Techniques," 2017 IEEE Sensors, 2017, pp. 1-3.
Clarke, W. L., "The Original Clarke Error Grid Analysis (EGA)," Diabetes Technol. & Ther., vol. 7, No. 5, pp. 776-779, 2005.
Dichristina, M. et al., "Top 10 Emerging Technologies of 2017," Scientific American, vol. 317,No. 6, pp. 28-39, 2017.
Ebden, M. "Gaussian Processes for Regression: A Quick Introduction," GPtutorial. pdf, 2008, 13 pages.
Evans, N. D. et al., "Non-Invasive Glucose Monitoring by NAD(P)H Autofluorescence Spectroscopy in Fibroblasts and Adipocytes: A Model for Skin Glucose Sensing," Diabetes Technol. & Ther., vol. 5, No. 5, pp. 807-816, 2003.
Federal Communications Commission, "Specific Absorption Rate (SAR) for Cellular Telephones," 2019. https://www.fcc.gov/general/specific-absorption-rate-sar-cellular-telephones, 2 pages, [Accessed on Mar. 1, 2022].
Gabbay, R. A. et al., "Optical Coherence Tomography-Based Continuous Noninvasive Glucose Monitoring in Patients with Diabetes," Diabetes Technol. & Ther., vol. 10, No. 3, pp. 188-193, 2008.
Gabbay, R. A., "New Developments in Home Glucose Monitoring: Minimizing the Pain," Canadian Journal of Diabetes, 2003;27(3):271-276.
Gerges, A. et al., "Tea catechins induce crosstalk between signaling pathways and stabilize mast cells in ulcerative colitis," Journal of Biological Regulators and Homeostatic Agents. vol. 31. 865-877 (2017), 14 pages.
Govind, G. et al., "Metamaterial-Inspired Microwave Microfluidic Sensor for Glucose Monitoring in Aqueous Solutions," IEEE Sens. J., vol. 19, No. 24, pp. 11900-11907, 2019.
Hanna, J. et al., "Noninvasive, wearable, and tunable electromagnetic multisensing system for continuous glucose monitoring, mimicking vasculature anatomy," Sci. Adv., vol. 6, No. 24, p. eaba5320, 2020, 11 pages.
Honn, K. V, et al., "Fetal Bovine Serum: a Multivariate Standard," Proc. Soc. Exp. Biol. Med., vol. 149, No. 2, pp. 344-347, 1975.
Jang, C. et al., "Non-Invasive Fluidic Glucose Detection Based on Dual Microwave Complementary Split Ring Resonators With a Switching Circuit for Environmental Effect Elimination," IEEE Sens. J., vol. 20, No. 15, pp. 8520-8527, 2020.
Jang, C. et al., "Temperature-Corrected Fluidic Glucose Sensor Based on Microwave Resonator," Sensors, vol. 18, No. 11, p. 3850, 2018. (12 pages).
Joubert, M. et al., "Personal continuous glucose monitoring (CGM) in diabetes management: review of the literature and implementation for practical use," Diabetes Res. Clin. Pract., vol. 96, No. 3, pp. 294-305, 2012.
Karacolak, T. et al., "Cole-cole model for glucose-dependent dielectric properties of blood plasma for continuous glucose monitoring," Microw. Opt. Technol. Lett., vol. 55, No. 5, pp. 1160-1164, 2013.
Keenan, D. B. et al., "Delays in Minimally Invasive Continuous Glucose Monitoring Devices: A Review of Current Technology," J. Diabetes Sci. Technol., vol. 3, No. 5, pp. 1207-1214, 2009.
Keysight Technologies, "FieldFox Handheld RF and Microwave Analyzers." https://www.keysight.com/us/en/products/network-analyzers/fieldfox-handheld-rf-microwave-analyzers, 8 pages. [Accessed on Mar. 8, 2022].
Kim, S et al., "Parylene coated waterproof washable inkjet-printed dual-band antenna on paper substrate." International Journal of Microwave and Wireless Technologies 10.7 (2018): 814-818, 5 pages.
Kost, J. et al., "Transdermal monitoring of glucose and other analytes using ultrasound," Nat. Med., vol. 6, No. 3, pp. 347-350, 2000.
Kovacs, G. et al., "Interactions of Electromagnetic Waves with Biological Tissue," Bioe 200C Spring, 2005, 47 pages.
Leal, Y. et al., "Real-Time Glucose Estimation Algorithm for Continuous Glucose Monitoring Using Autoregressive Models," J. Diabetes Sci. Technol., vol. 4, No. 2, pp. 391-403, 2010.
Lee, S. et al., "Glucose measurements with sensors and ultrasound," Ultrasound Med. & Biol., vol. 31, No. 7, pp. 971-977, 2005.
Lipani, L. et al., "Non-invasive, transdermal, path-selective and specific glucose monitoring via a graphene-based platform," Nat. Nanotechnol., vol. 13, No. 6, pp. 504-511, 2018, 10 pages.
Liu, W. et al., "A Transmission-Reflection Method for Complex Permittivity Measurement Using a Planar Sensor," IEEE Sens. J., vol. 18, No. 10, pp. 4059-4065, 2018.
Overland, J. et al., "Improving Self-Monitoring of Blood Glucose among Adults with Type 1 Diabetes: Results of the MobileTM Study," Diabetes Ther., vol. 5, No. 2, pp. 557-565, 2014.
Philips, "Skin Surface Temperature Probe disposable, sterilized, continuous monitoring." https://www.usa.philips.com/healthcare/product/HC21091A/skin-surface-temperature-probe-disposable--sterilized--continuousmonitoring-sensor, 4 pages [Accessed on Mar. 1, 2022].
Pleus, S. et al., "Performance evaluation of a continuous glucose monitoring system under conditions similar to daily life," J Diabetes Sci Technol. Jul. 1, 2013;7(4):833-41.
Rasmussen, C. E., "Gaussian Processes in Machine Learning," In: Bousquet O., von Luxburg U., Rätsch G. (eds) Advanced Lectures on Machine Learning. ML 2003. Lecture Notes in Computer Science, vol. 3176. Springer, Berlin, Heidelberg, 2003, pp. 63-71, Abstract only (2 pages).
Roche Diagnostics GMBH, "Accu-Chek Active blood glucose meter." [Online]. Available: https://www.rochediabetescareme.com, 2014, 1 page [Accessed on Mar. 8, 2022].
Saha, S. et al., "A Glucose Sensing System Based on Transmission Measurements at Millimetre Waves using Micro strip Patch Antennas," Sci. Rep., vol. 7, No. 1, pp. 1-11, 2017.
Seeed Studio, "Grove—GSR sensor." https://www.seeedstudio.com/Grove-GSR-sensor-p-1614.html. , 4 pages [Accessed on Mar. 1, 2022].
Sieg, A et al. "Noninvasive glucose monitoring by reverse iontophoresis in vivo: application of the internal standard concept." Clin Chem. Aug. 2004;50(8):1383-90.
SO,C.-F. et al., "Recent advances in noninvasive glucose monitoring." Medical devices (Auckland, N.Z.) vol. 5 (2012):45-52.
Texas Instruments, "CC2650STK SimpleLink? Bluetooth low energy/Multi-standard SensorTag." [Online]. Available: https://www.ti.com/tool/CC2650STK, 4 pages [Accessed on Mar. 1, 2022].
Vashist, S. K., "Non-invasive glucose monitoring technology in diabetes management: A review," Anal. Chim. Acta, vol. 750, pp. 16-27, 2012.
Velez, P. et al., "Microwave Microfluidic Sensor Based on a Microstrip Splitter/Combiner Configuration and Split Ring Resonators (SRRs) for Dielectric Characterization of Liquids," IEEE Sens. J., vol. 17, No. 20, pp. 6589-6598, 2017.
Wagner, J. et al., "Invasiveness as a Barrier to Self-Monitoring of Blood Glucose in Diabetes," Diabetes Technol. & Ther., vol. 7, No. 4, pp. 612-619, 2005.
Webb, R. C. et al., "Ultrathin conformal devices for precise and continuous thermal characterization of human skin," Nat. Mater., vol. 12, No. 10, pp. 938-944, 2013.

(56) References Cited

OTHER PUBLICATIONS

Yanamadala, J. et al., "New VHP-Female v. 2.0 Full-Body Computational Phantom and Its Performance Metrics Using FEM Simulator ANSYS FEM," in 2015 37th Annual International Conference of the IEEE Engineering in Medicine and Biology Society (EMBC), 2015, pp. 3237-3241.

Yilmaz, T. et al., "Radio-Frequency and Microwave Techniques for Non-Invasive Measurement of Blood Glucose Levels," Diagnostics, vol. 9, No. 1, p. 6, 2019, 34 pages.

* cited by examiner

Terminal S Parameter Plot 59 Design199

| Name | X | Y |
| --- | --- | --- |
| m1 | 0.9025 | -23.840 |
| m2 | 3.1075 | -34.284 |
| m3 | 3.6850 | -43.510 |

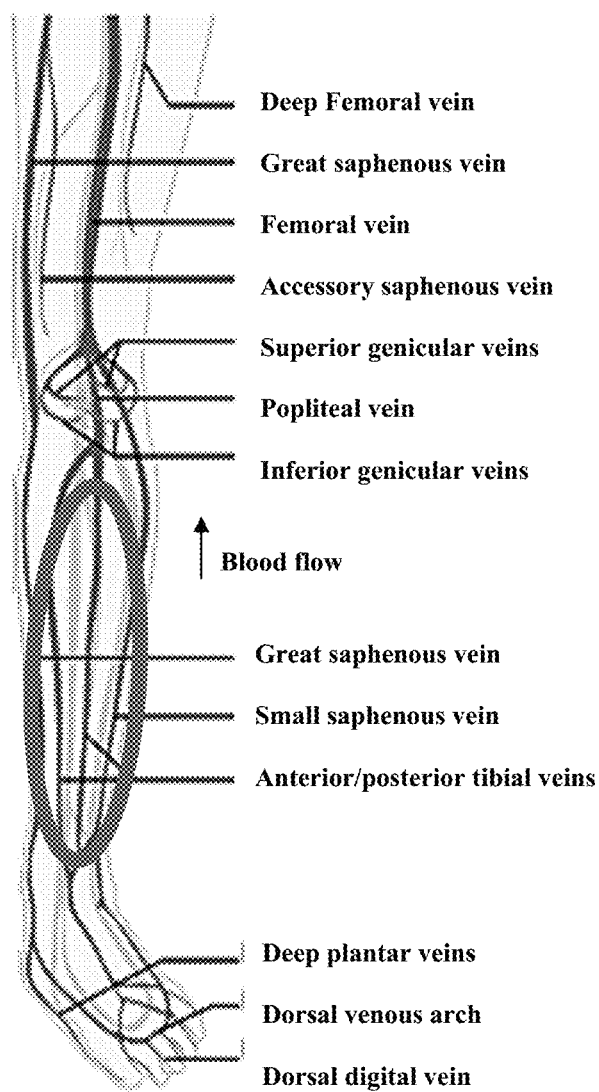 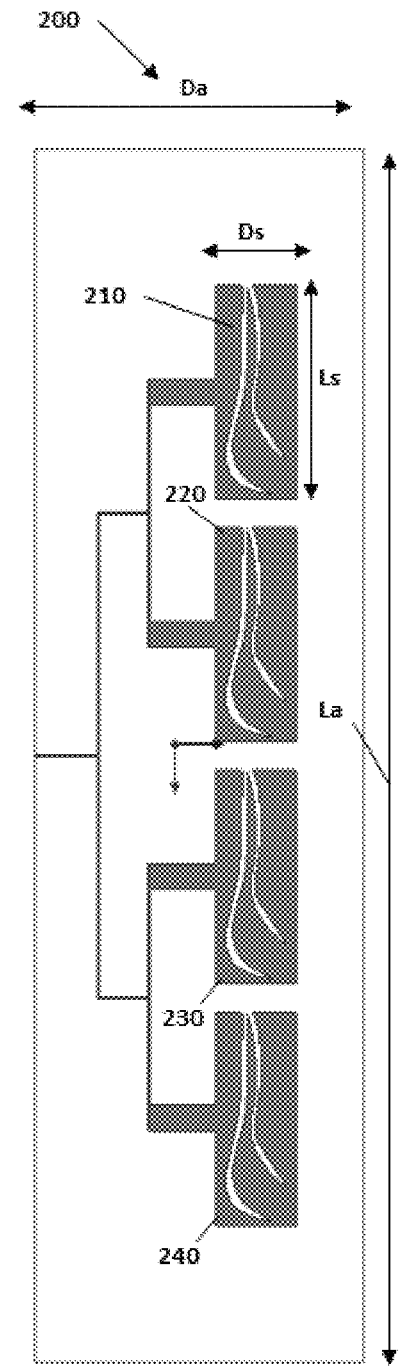
FIG. 2
FIG. 3A

ANTENNA ARRAY OR A GROUP OF ANTENNA ELEMENTS FOR BIOMARKER MONITORING, NERVE STIMULATIONS AND METHODS OF USE

CROSS-REFERENCE TO RELATED APPLICATIONS

The present applications claims priority from U.S. provisional application Ser. No. 63/057,624, filed Jul. 28, 2020, herein incorporated by reference in its entirety.

BACKGROUND

The invention generally relates to antennas and monitoring devices.

Many research groups have studied the potential of a radio frequency reflectometry technique in measuring blood glucose levels. Buford Randall Jean and Eric C, Green at Baylor University explored the usage of antennas to estimate the glucose levels. They tested different antenna's design and the results of regular blood and modified Blood composition for each sensor were compared. The best design was chosen upon the max shift of S11 and S21 with change in blood permittivity. The Single Spiral Micro-strip designed to resonant at 1.5 GHZ shows changes in its response when exposed to materials with different permittivity.

Another RF system was developed by J. Venkataraman and M. Sidley from Rochester Institute of Technology. Their device consists of a microstrip antenna mounted on the patient's arm. During their early research, they tested three different types of antennas in order to determine which one would deliver the best results in terms of monitoring the variations of the glucose levels. First a spiral and serpentine antenna were designed at 2.45 GHz and tested. Later, a planer dipole was developed with a resonate frequency at 1.4 GHz which outperform the two previous designs. They were able to achieve a shift of 1 MHz in resonate frequency for a shift of 14.62 mg/dl in glucose concentration.

Jinjin Shao et al. proposed a four-arm spiral microstrip antenna to detect the variation of glucose concentration. It's designed to resonate at 5 GHz with a very narrow bandwidth. They tested their sensor using a finger model in HFSS by varying its relative permittivity with a step of 0.01. A very small frequency shift was achieved by their sensor. M. S. Ali et al. investigated another RF sensor to monitor the glucose variation. They designed an ultra-wide band rectangular patch antenna resonating at 4.7 GHz with a bandwidth of 8.77 GHz ranging from 3.23 to 12 GHz and a gain of 6.09 dB. Their sensor composed of two UWB planar antennas and a signal processing technique based with an artificial neural network to predict the glucose levels.

H. C. Garcia et al. [8], in collaboration with mediwise, designed other nomnvasive techniques. The sensor is composed of two rectangular microstrip patch antennas with dimensions of 1.5 by 1.5 mm designed to resonant at 60 GHz. The sensor was utilized to monitor several concentrations of water-based glucose-loaded liquid samples enclosed in an acrylic tank. Recently they tested their sensing device on patents during in-vivo Intravenous Glucose Tolerance Test (IVGTT). They were able to detect a sensitivity of 1.33 mmol/l (24 mg/dl) in water-based glucose-loaded liquid samples and 4 mmol/l (=72 mg/dl) in clinical trials. The present invention attempts to solve these problems as well as others.

SUMMARY OF THE INVENTION

Provided herein are systems, methods and apparatuses for an Antenna Design for Biomarker Monitoring.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

BRIEF DESCRIPTION OF THE DRAWINGS

In the accompanying figures, like elements are identified by like reference numerals among the several preferred embodiments of the present invention.

FIG. 2 is a display of the leg vein and the Peroneal venae comites and Posterior tibial venae comites.

FIG. 3A is a schematic showing the sensor array according to one embodiment.

DETAILED DESCRIPTION OF THE INVENTION

Figure 1A:
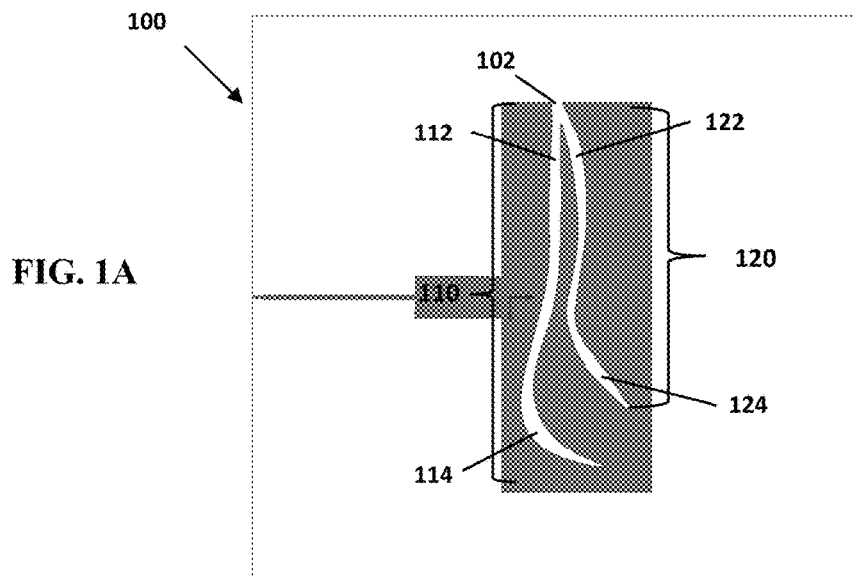
FIG. 1A is a schematic representing the antenna sensor and the feeding line.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The Antenna Design for Biomarker Monitoring measures biological and chemical markers and tracers in blood including glucose concentration without any extraction of blood. The Antenna Design for Biomarker Monitoring comprises a non-invasive method using Radio Frequency and Antenna Circuits and Systems. The Antenna Design for Biomarker Monitoring is a wearable device that can be a glove, semi-glove, or sock, or any similar wearable device that can non-invasively measure these blood physiological Biomarker, such as glucose levels in an instantaneous manner and continuous manner.

The device and design continuously measures biological, chemical markers and other tracers in the blood stream for physiological and pathophysiological screening in health and in disease in a non-invasive manner. Biomarkers can include novel/foreign/malignant or non-malignant cells or other newly developed molecules that may not be part of the typical constituents of the biological system. Biomarkers can also be traced not only in blood, but in the rest of the biological system, such as saliva, tissue, and the like.

Biomarkers as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Biomarkers can include naturally occurring substances, artificial substances, metabolites, and/or reaction products. In some embodiments, the Biomarkers for measurement by the sensor heads, devices, and methods is a Biomarker. However, other Biomarkers are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; pro-BNP; BNP; troponin; carnosinase; CD4; ceruloplasmin; chenodeoxycholic acid; chloroquine; cholesterol; cholinesterase; conjugated 1-hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-I, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free-human chorionic gonadotropin; free erythrocyte porphyrin; free thyroxine (FT4); free tri-iodothyronine (FT3); fumarylacetoacetase; galactose/gal-I-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase 1; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute Biomarkers in certain embodiments. The Biomarkers can be naturally present in the biological fluid, for example, a metabolic product, a hormone, an antigen, an antibody, and the like. Alternatively, the Biomarkers can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocame (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated Biomarkers. Biomarkers such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

An example of pathophysiological alteration leading to diseases include, but are not limited to, hyperglycemia/diabetes, cholesterolemia, heart disease. Biomarkers as well as other biological alterations that involve measuring variations of glucose level, cholesterol levels, Pro-BNP (pro-Brain Natriuretic peptide) and troponin levels, and other molecular Biomarkers in living tissue. For example in diabetes, the proposed prototype is envisioned to help monitor instantaneous glucose levels to be used: to determine the alteration in glycemia and variations from norm; and for autonomous interventions such as insulin injections; and to offer diabetic patients an improved and self-constrained control of the disease. Thus, along with an estimate of the bulk concentration, the device monitors the rate of change of concentrations to predict possible hyperglycemia and hypoglycemia early.

The embodiments disclosed herein measures biological and chemical markers and tracers in blood including and not restricted to glucose concentration without any extraction of blood. The non-invasive method using Radio Frequency and Antenna Circuits and Systems is a wearable device that can be a sock, or any similar wearable device that can non-invasively measure these blood physiological markers in an instantaneous and continuous manner.

The sensor comprises an antenna array with a certain number of elements or a group of antenna elements that are biologically configured by the arteries and veins, and/or nerves in a specific location of the human body. The sensor can be used to stimulate specific nerves for treatment, muscle spasms, pain management of peripheral neuropathy, and other applications of noninvasive nerve stimulation or monitoring using the same frequencies and same power level used for glucose monitoring.

The antenna array or the group of antenna elements can be homogeneous, heterogeneous, uniform or non-uniform in order to adapt to the specific location in the human anatomy or vasculature.

For one embodiment, the antenna elements or array elements are biologically configured by the arteries and veins in the lower leg to non-invasively detect the concentration of blood constituents in human blood stream continuously through electromagnetic wave radiation. Blood constituents include and are not restricted to glucose, cholesterol, lactate and many others.

In another embodiment, the antenna elements or array elements are configured by the nerve topology can be used to stimulate specific nerves for treatment, muscle spasms, pain management of peripheral neuropathy, and other applications of noninvasive nerve stimulation or monitoring.

In another embodiment, the antenna elements or array elements are configured by both the nerve topology and artery or vein topologies for both blood constituents monitoring and nerve stimulations, were parts of the element target the vasculature network and other parts of the same elements target the nerve topology. The power and frequency used for the nerve monitoring and stimulation are the same range of frequencies as for biomarker monitoring between about 0.5 GHz and about 4 GHz and the same power level (SAR limits=1.6 W/kg).

In another embodiment, elements in the sensor mirror the shape of the Peroneal venae comites and Posterior tibial venae comites. In one embodiment, the sensor is used to transmit electromagnetic waves into human tissues in areas in close proximity to the main venae comites veins in order to better monitor and detect the variation of the concentration of the blood constituents compared to other embodiments that do not track the vein structure. In one embodiment the sensor slots correspond to the Anterior Tibial venae comities and the Posterior Tibial venae comities.

In another embodiment, the elements of the antenna array or the group of antenna elements comprised of homogeneous uniform or nonuniform array elements with topology that best track the underlying targeted vasculature or nerve anatomy. In another embodiment, a group of heterogeneous antenna elements in a uniform or nonuniform array with a topology that match the targeted underlying vasculature or nerve anatomy are designed.

In another embodiment, the elements of the antenna array or the group of antenna elements are composed of wire antennas, loop antennas, broadband antennas, traveling wave antennas, frequency independent, miniature, fractal, aperture, micro-strip patch, tunable (active), reconfigurable, passive, or integrated antennas.

In another embodiment, the antenna array topology or configuration comprise any distribution, including, but not limited to: linear, planar or circular distribution.

In another embodiment, the antenna array or the group of antenna elements are disposed on textile or any other type of substrates to constitute a sock or any type of wearable or clothing apparel.

In another embodiment, the antenna designs operate at different frequency bands including, below or above UHF and Microwave, an example can be mm-wave region.

In another embodiment, the antenna array or the group of antenna elements are composed of at least 4 sensor elements or at least 4 distinct sensor elements with different slot designs or slot configurations. The antenna array or group of antenna elements are operational at multiple frequencies within the microwave region. Specifically, the antenna is designed to operate in the UHF, L- and lower S-bands ranging between 500 MHz and 4 GHz.

In another embodiment, the antenna array or group of antenna elements are disposed on a flexible dielectric substrate to be placed easily into a sock or leg fitting.

In another embodiment, the elements of the antenna array or the group of antenna elements are a micro-strip patch antennas comprised of a web of slots that represent the human lower leg veins. In one embodiment, the array elements are comprised of homogeneous or identical slots that best track the underlying targeted vasculature anatomy. In another embodiment, a group of antenna elements with non-identical slots match the targeted underlying vasculature anatomy are designed.

In other embodiments, the slot designs are adjusted to fit the physiology of multiple users by relying on stretchable antenna material. For example, a sock along with embedded stretchable antenna array can stretch to fit the topology of the veins of the specific user.

In another embodiment, the signal measured from the antenna array or group of antenna elements is converted using a computer program that allows the transformation of the magnitude and the phase of the reflected and/or transmitted signals into concentration of the blood constituents via trained models.

Figure 1B:
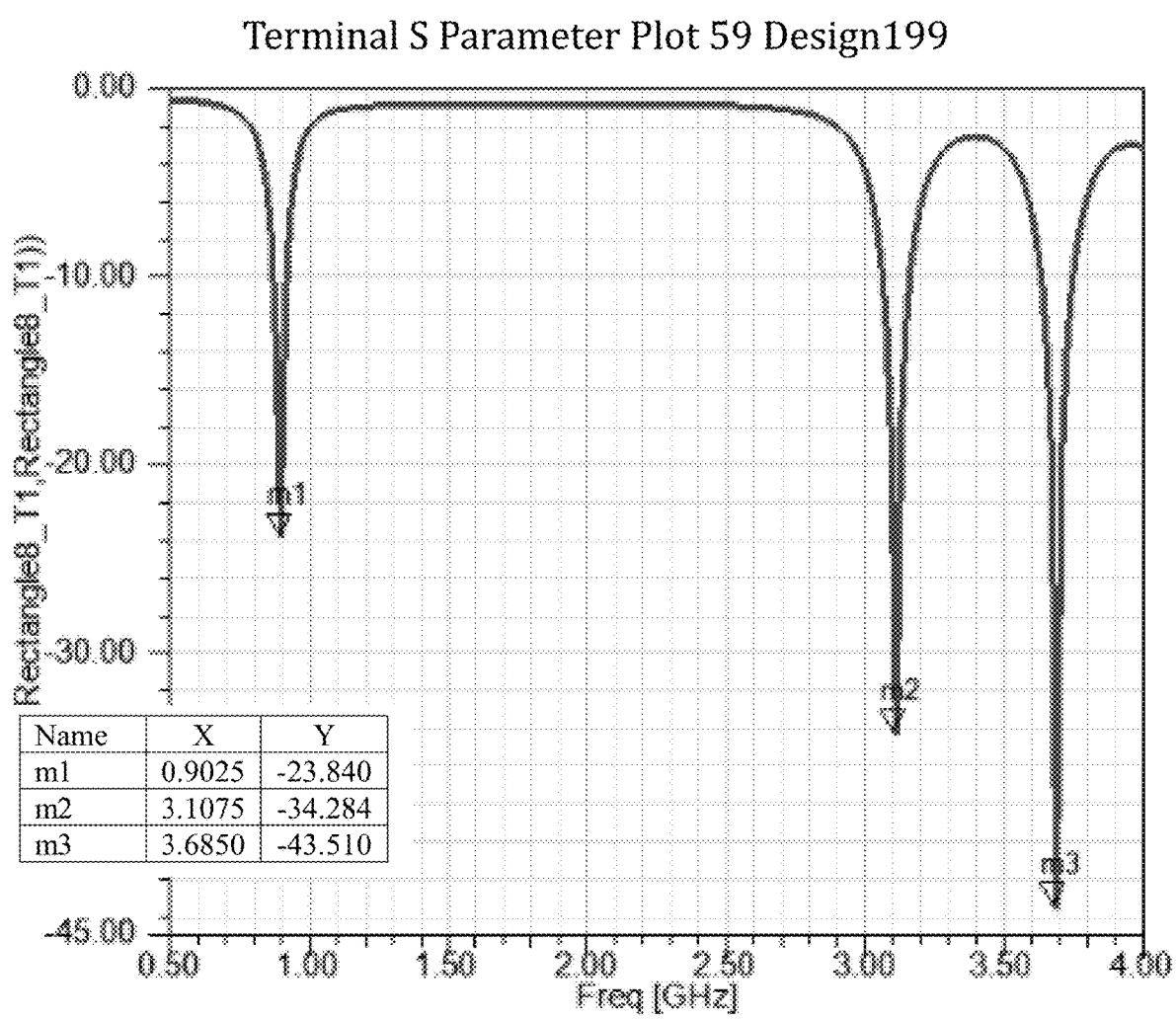
FIG. 1B is a graph of the terminal S parameter plot of FIG. 1A.

The Antenna Design for Monitoring comprises a sensor 100, as shown in FIG. IA, composed of an antenna including a plurality of slots corresponding to the arteries and veins of a human leg to non-invasively detect the concentration of blood constituents in human blood stream continuously through electromagnetic wave radiation, according to one embodiment. In other embodiment, the antenna design may include a plurality of slots corresponding to arteries and veins in other anatomical structures, such as the foot, arm, leg, neck, and the like. The correspondence between the slots and underlying vein structures allows to the antenna to focus/strengthen the sensing mechanism to a plurality of key blood vessels structures while minimizing the direct interaction with noncritical areas. Hence, the sensitivity of the sensor to blood constituent variations in the underlying vessels is increased. The sensor 100 comprises a first slotted arch 110 and a second slotted arch 120. The first slotted arch 110 and the second slotted arch 120 are directly connected through a top slot 102. The first slotted arch 110 corresponds to the shape of the Peroneal venae comites, and the second slotted arch 120 corresponds to the shape of Posterior tibial venae comites. The first slotted arch 110 includes a long slotted main branch 112 connected to a distal curvilinear branch 114. The distal curvilinear branch 114 may include an angle of curvature between about 55 degrees and about 120 degrees. The long slotted main branch 112 connects to the top slot 102, which is a substantially V-shape, all of which corresponds to the shape of the Peroneal venae comites or the lateral perforating veins, as shown in FIG. 2. The second slotted arch 120 includes a second long main branch 122 that correspond to the Posterior tibial venae comites or the anterior tibial venae comites. The second long main branch 122 includes a second distal curved branch 124. In one embodiment, the first slotted arch 110 is the Peroneal venae comites slot including a length of about 25 mm and a slot width: between about 0.5 mm and about 1 mm. In one embodiment, the second slotted branch 120 is the Posterior tibial venae comites slot including a length of about 21 mm and a slot width: between about 0.5 mm and about 1 mm. In one embodiment, the antenna is used to transmit electromagnetic waves into human tissues in areas in close proximity to the veins in order to better monitor and detect the variation of the concentration of the blood constituent compared to other embodiments that do not track the vein structure. The sensor 100 as shown in FIG. 1A includes a dielectric constant $\varepsilon_r$ is about 2.99, as shown in FIG. 1B. Dielectric constant ($\varepsilon_r$) is defined as the ratio of the electric permeability of the material to the electric permeability of free space (i.e., vacuum) and its value can derived from a simplified capacitor model.

According to some embodiments, the slots may include a range of geometries, angles, and lengths for all the different branches. A range of the widths of the slots, and spacing between the slots, may be provided if slot/design modification is required. The stretching involves stretching the spaces between two slots and/or angle between two slots as well to better overlap the slots and targeted underlying vein. The specific desired ranges for the slots/spacings will be divided into groups. Otherwise, the variation in the design upon stretching would be large if it were to cover all desired ranges. The slot designs may be grouped into several size categories such as extra small, small, large, and extra-large, depending the size of the target underlying anatomy. Flexibility in one embodiment allows for matching in between the standard sizes. Flexibility in another embodiment allows for matching based on visual and measurement calibrations. In one embodiment, the design may be customized and stretchable for children, where the stretching enhances the coverage of the veins. Flexibility then allows in this embodiment stretching the product as the child grows over a period of several months. Flexibility includes a value between about 0.1 Gpa to about 10.0 Gpa. Polydimethylsiloxane (PDMS), Poly(ethylene terephthalate) (PET), polyimide (PI) and parylene, which has superior flexibility, malleability, may be used as the substrate for the flexible sensor.

The Peroneal venae comites and the Posterior tibial venae comites, are shown in FIG. 2. The slot width may correspond to the diameters of the respective Peroneal venae comites, the Posterior tibial venae comites, or the anterior tibial venae comites. The Peroneal venae comites include a slot width in the range of about 0.5 mm to about 1.5 mm. The Posterior tibial venae comites includes a slot width in the range of about 0.5 mm to about 1.5 mm.

Figure 3B:
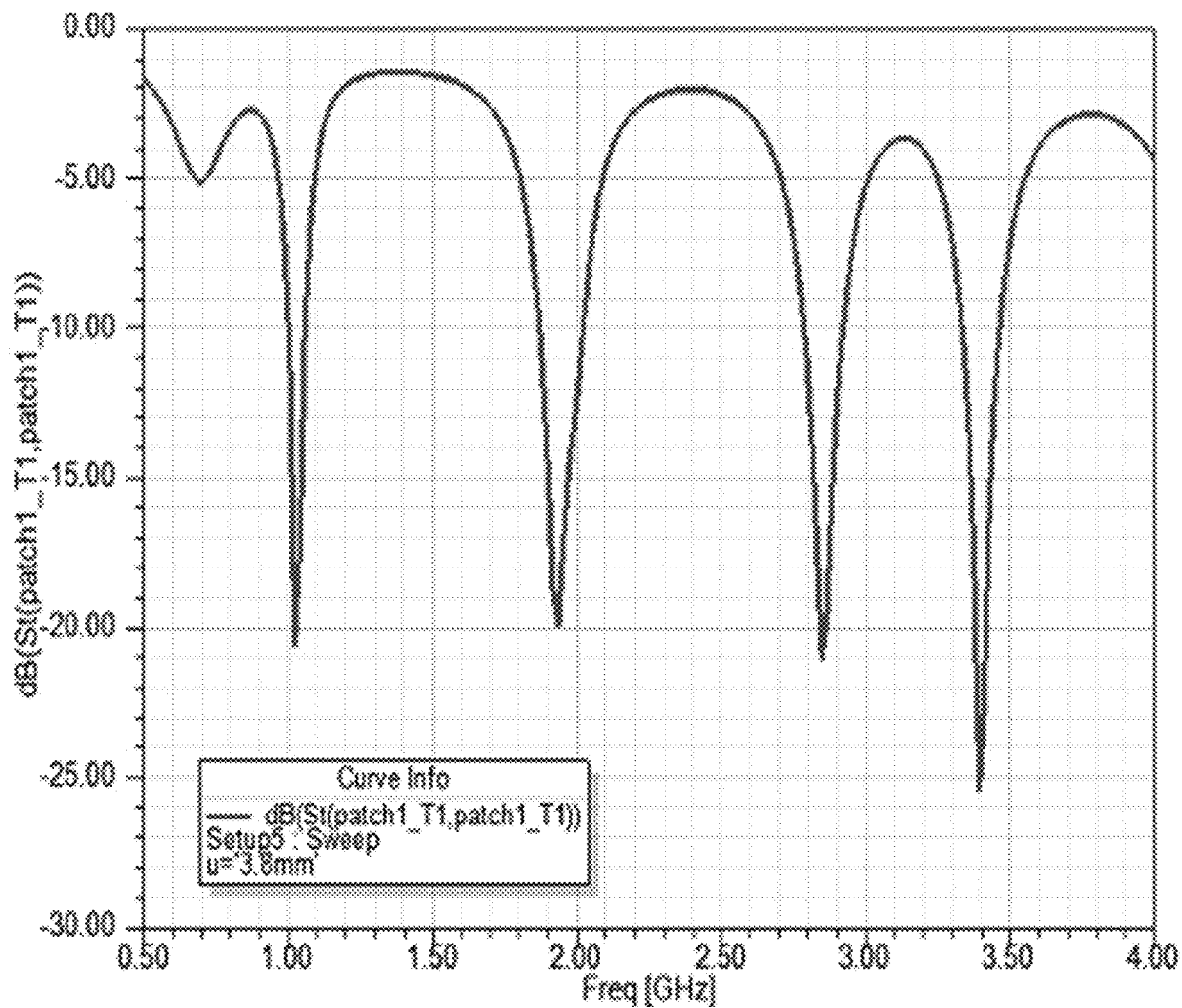
FIG. 3B is a graph of the terminal S parameter plot of FIG. 3A.

In one embodiment, the sensor comprises an antenna array 200 with a certain number of elements or a group of antenna elements 100 corresponding sensor diameter Ds is in range of about 10.0 mm to about 17.0 mm and a sensor length Ls between about 25.0 mm to about 35 mm for proper coverage of the veins, as shown FIG. 3A. In one embodiment, the dimensions for the antenna array 200 include an array diameter Da is in the range of about 45.0 mm to about 65.0 mm, and an array length La in the range of about 155 mm to about 190 mm, which may approximate a typical small size adult female. In this embodiment, the sensor array 200 comprises a first slotted sensor 210, a second slotted sensor 220, a third slotted sensor 230, and a fourth slotted sensor 240. The first slotted sensor 210, the second slotted sensor 220, the third slotted sensor 230, and the fourth slotted sensor 240 may be identical, uniform, or heterogeneous. The first slotted sensor 210, the second slotted sensor 220, the third slotted sensor 230, and the fourth slotted sensor 240 may include a slot width of about 1.6 mm. The first slotted sensor 210, the second slotted sensor 220, the third slotted sensor 230, and the fourth slotted sensor 240 include a first slotted arch 110 and a second slotted arch 120 directly connected to the first slotted arch 110 through a top slot 102. The first slotted arch 110 corresponds to the shape of the Peroneal venae comites, and the second slotted arch 120 corresponds to the shape of Posterior tibial venae comites. Further modifications to the first slotted sensor 210, the second slotted sensor 220, the third slotted sensor 230, and the fourth slotted sensor 240 can be obtained from human measurements to define standard sizes for the Peroneal venae comites and the Posterior tibial venae comites. The sensor array 200 as shown in FIG. 3A includes a $\varepsilon_r$ is about 2.99 as shown in FIG. 3B.

In one embodiment, the antenna is a micro-strip antenna comprised of a web of slots that represent the human leg veins. The antenna is designed using a flexible dielectric substrate to be placed easily into a leg covering. In another embodiment, the antenna slots can be designed after the foot veins, and can be built on a flexible substrate to fit into a sock. The antenna comprises a spirally shaped feeding transmission line with three turns in a spiral configuration that are positioned on the bottom layer of the antenna such that the transmission line is separated from the sensing surface. The spirally shaped feeding line enhances the coupling between the feedlines and the slots on the top layer of the antenna. The antenna resonates when it is loaded with a typical human leg tissue to increase its sensitivity to the variation of the blood constituents. The human leg tissue comprises a skin layer, fat layer, blood layer, muscle layer and bone layer. The antenna is operational at multiple frequencies within the microwave region. Specifically, the antenna is designed to operate above or below UHF, L-bands and lower S-bands ranging between about 500 MHz and about 3 GHz, alternatively in the microwave, an example can be mm-wave region.

In one embodiment, the antenna is designed to be multiband, where each component of the antenna is designed after Peroneal venae comites and Posterior tibial venae comites. The spiral feeding line allows different slots to be active and hence also enhances the multi-band behavior of the antenna. The antenna in another embodiment is designed to be reconfigurable to cover multiple frequencies within the frequency band ranging from about 500 MHz and about 3 GHz. The reconfiguration of the antenna is restrained to its frequency of operation by resorting to various reconfiguration components such as pin diodes, RF MEMs, varactors, and/or digitally tunable capacitors. The reconfiguring component will be positioned in strategic locations along the slots or the feeding line of the antenna. In another embodiment, mechanical reconfiguration techniques can also be used to reconfigure the frequency of operation of the antenna. Such techniques include actuators, piezo-electric transducers, and others in order to change the separation between the ground planes and the slots or to change the lengths of the slot web or feeding lines through stretching of the material composing the antenna as well as other means.

In other embodiments, the design can be adjusted to fit the physiology of multiple users by relying by relying on stretchable antenna material. For one embodiment, a sock along with embedded stretchable antenna can stretch to fit the topology of the Peroneal venae comites and Posterior tibial venae comites of the specific user. In addition, the sock can be equipped with electro-mechanical peripheral circuitry to assist with the stretching or bending of the antennamtopology to match the human anatomy. The fitting stretching can be assisted by human eye, medical expert, or automatically via feedback from vein detection circuitry. The vein detection will be based on optical sensors, the vein images will be processed and the electromechanical circuitry will automatically adjust the stretchable antenna to match the underlying image.

In one embodiment, the stretchable antenna material similar to [1] TY-JOURAU-Chen, ZhiboAU-Xi, JingtianAU-Huang, WeiAU-Yuen, Matthew M. F.PY-2017DA-2017/09/08TI-Stretchable conductive elastomer for wireless wearable communication applications JO-Scientific Reports SP-10958VL-71S-1AB] can be used in one embodiment.

The above embodiments tune the design for random customers and hence fit the design better to different population groups. Variation of material upon stretching may be analyzed and expanded.

In one embodiment, the stretching is limited to be 10% over the width and length of the slot, since there is an effect of stretching both dielectric and conductive material on the efficiency, resonant frequency and matching of the device. As such, no more than 10% of stretching over the width or length of the slot is allowed. Based on TY-JOURAU-Chen, ZhiboAU-Xi, JingtianAU-Huang, WeiAU-Yuen, Matthew M. F.PY-2017DA-2017/09/08TI-Stretchable conductive elastomer for wireless wearable communication applications JO-Scientific Reports SP-10958VL-71S-1 AB, the radiation efficiency around the initial resonance frequency shifts monotonically as the stretching percentage increases. With the increasing strain, the resonance frequency shifts to a lower frequency due to the increased effective electrical length. The Ag-PDMS conductor can be considered as hyperelastic material; therefore, when the antenna is elongated in the length direction, the width and height shrink proportionally to keep the total volume constant during deformation, resulting in reduced impedance match and hence lower radiation efficiency.

The design tolerance to stretching can be altered in some embodiments, as follows: (a) Tolerating impedance match reduction: this can be tolerated as long as the stretched antenna maintains resonance levels are maintained moderately below −10 db. Hence, the design is configured to maintain resonance levels below −10 db under maximum stretching conditions (b) Tolerating Lower radiation efficiency upon stretching: this can be tolerated to a certain extent, and can be resolved by increasing the input power. (c) Tolerating changed response of the stretched design: This does not have implications on the sensitivity measurements, or glucose level tracking, since the stretched design will be used to measure the reference glucose level and the variations. The model is developed independently for the stretched design.

Figure 4A:
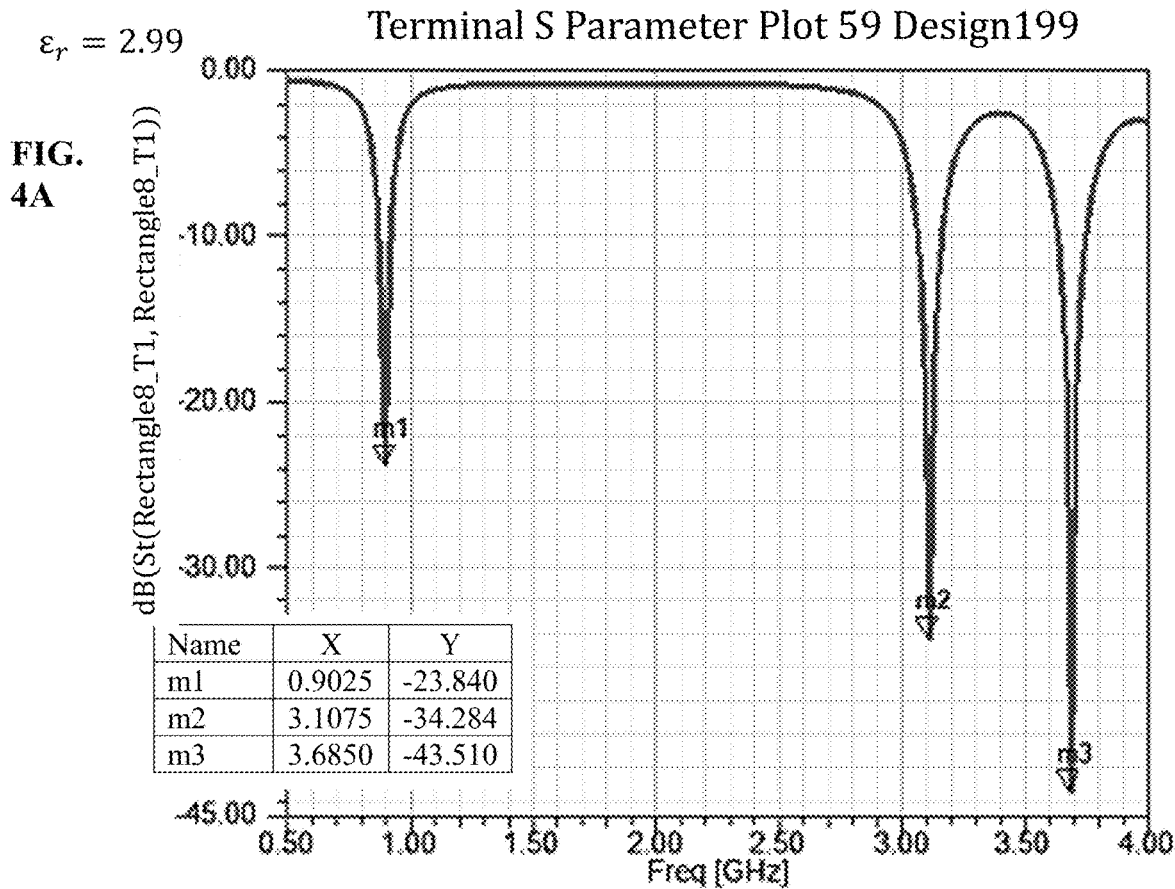
FIGS. 4A-4B are terminal S parameter plots of the signal antenna element 100 including a range of Eris about 2.99 and $\varepsilon_r$ is about 2.33, respectively.
Figure 4B:
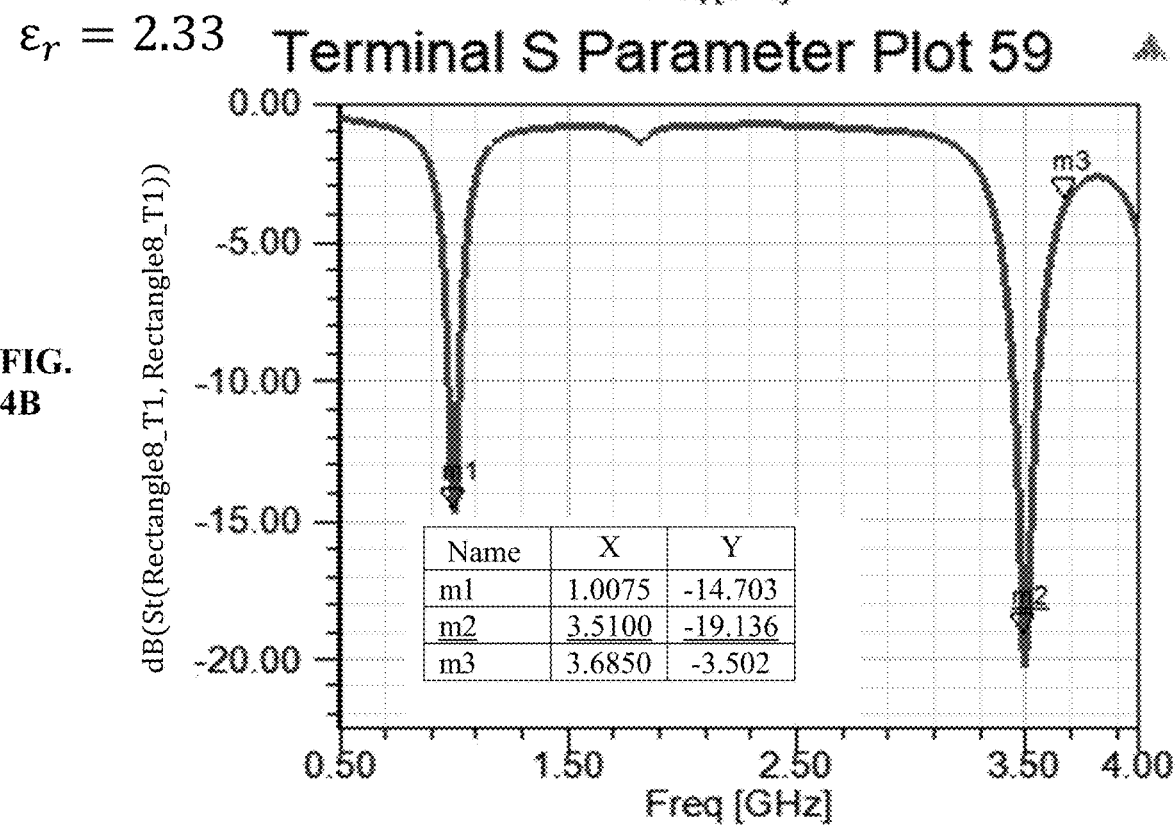

In another embodiment, as shown in FIGS. 4A-4B, an antenna 100 including one element corresponding to the arteries and veins of a human leg to non-invasively detect the concentration of blood constituents in human blood stream continuously through electromagnetic wave radiation, according to one embodiment. The antenna including one element includes a range of εr is about 2.99 and εr is about 2.33.

Figure 5:
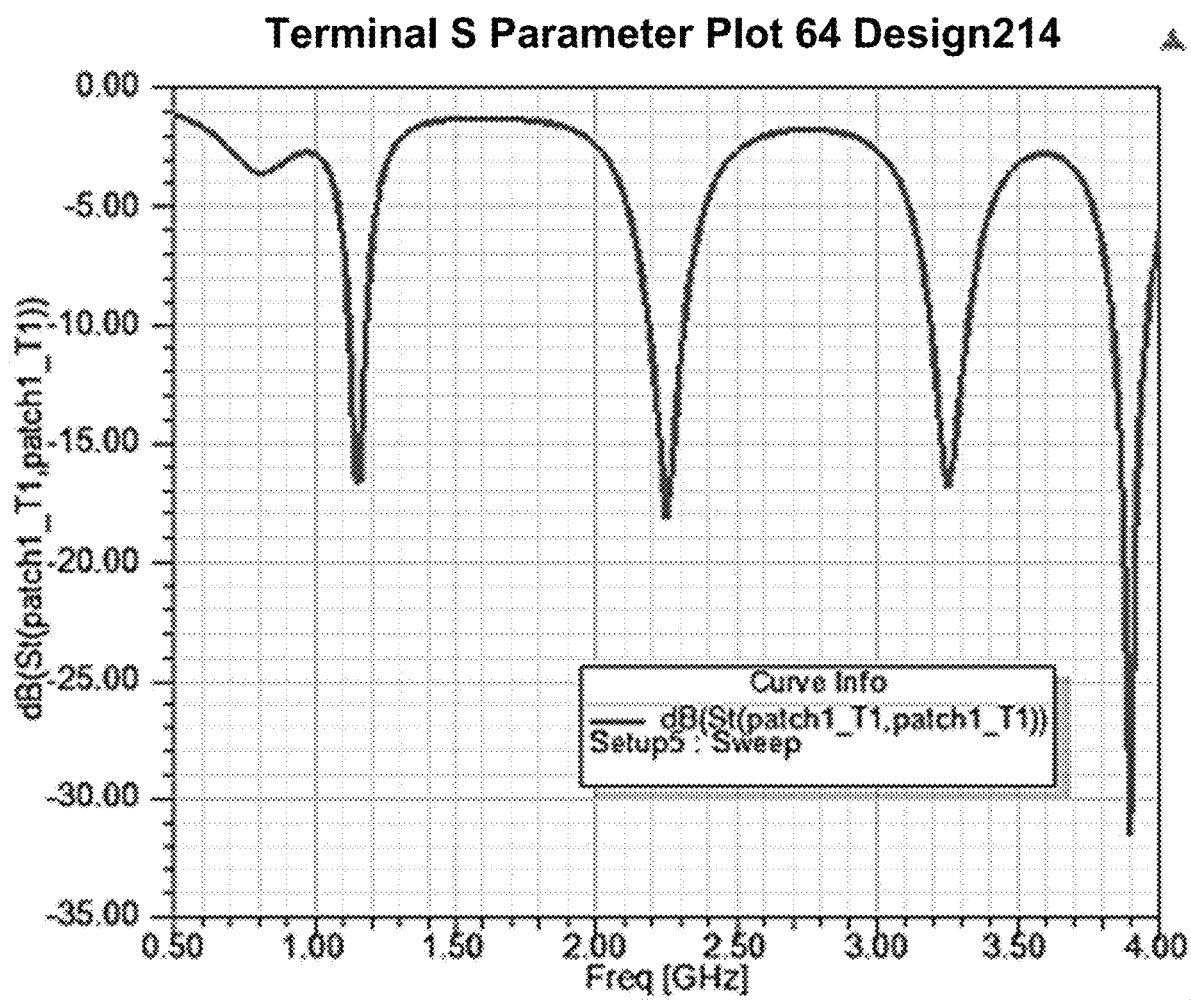
FIG. 5 is a graph of the terminal S parameter of the antenna array 200 including at least four sensor elements corresponding to a sensitivity of about $\varepsilon_r$ is about 2.33.

In another embodiment, as shown in FIG. 5, an antenna array 200 including at least four sensor elements corresponding to the arteries and veins of a human leg to non-invasively detect the concentration of blood constituents in human blood stream continuously through electromagnetic wave radiation. The antenna array 200 including at least four elements includes a sensitivity of about εr is about 2.33.

Figure 6A:
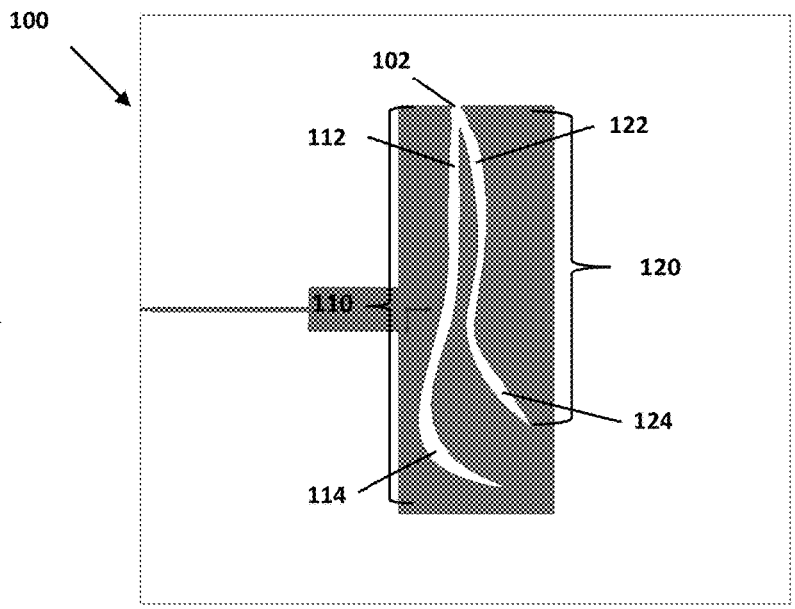
FIG. 6A is a schematic showing a longer sensor element embodiment.
Figure 6B:
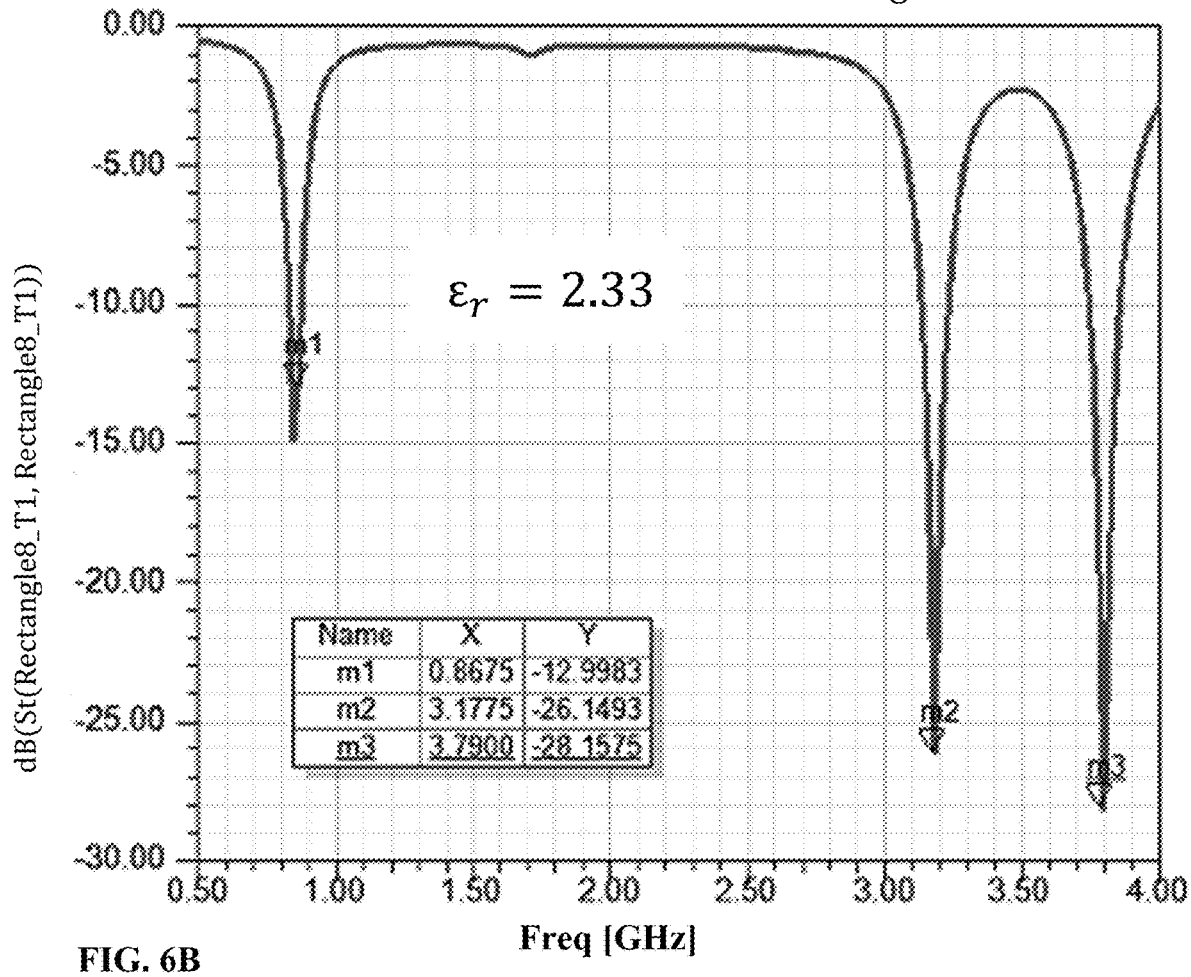
FIG. 6B is a graph of the terminal S parameter plot of FIG. 6A.

In another embodiment, the sensor 100 comprises a longer configuration for the length Ls of the sensor 100, as shown in FIG. 6A. The sensor including the first slotted arch 110 and the second slotted arch 120 directly connected through a top slot 102. The first slotted arch 110 includes a longer slotted main branch 112 extending substantially length of the substrate 108. The distal curvilinear branch 114 may include an angle of curvature between about 55 degrees and about 120 degrees. The long slotted main branch 112 connects to the top slot 102, which is a substantially V-shape, all of which corresponds to the shape of the Peroneal venae comites or the lateral perforating veins. The second slotted arch 120 includes a second long main branch 122 that correspond to the Posterior tibial venae comites or the anterior tibial venae comites. The second long main branch 122 includes a second distal curved branch 124. The sensor 100 includes a sensitivity of about εr is about 2.33, as shown in FIG. 6B.

Figure 7A:
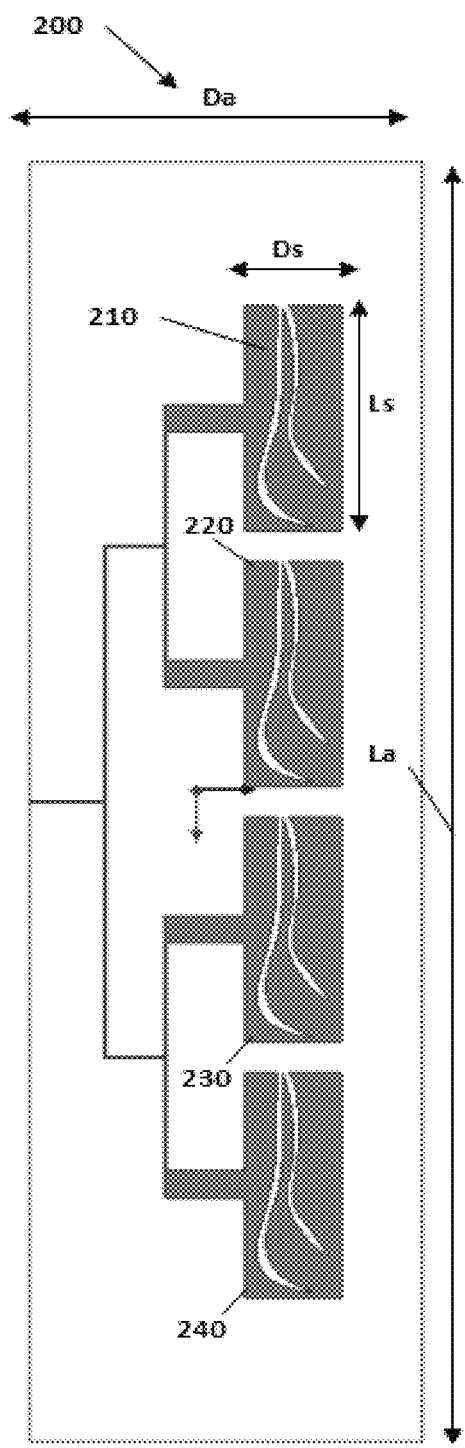
FIG. 7A is a schematic showing a longer sensor array embodiment.
Figure 7B:
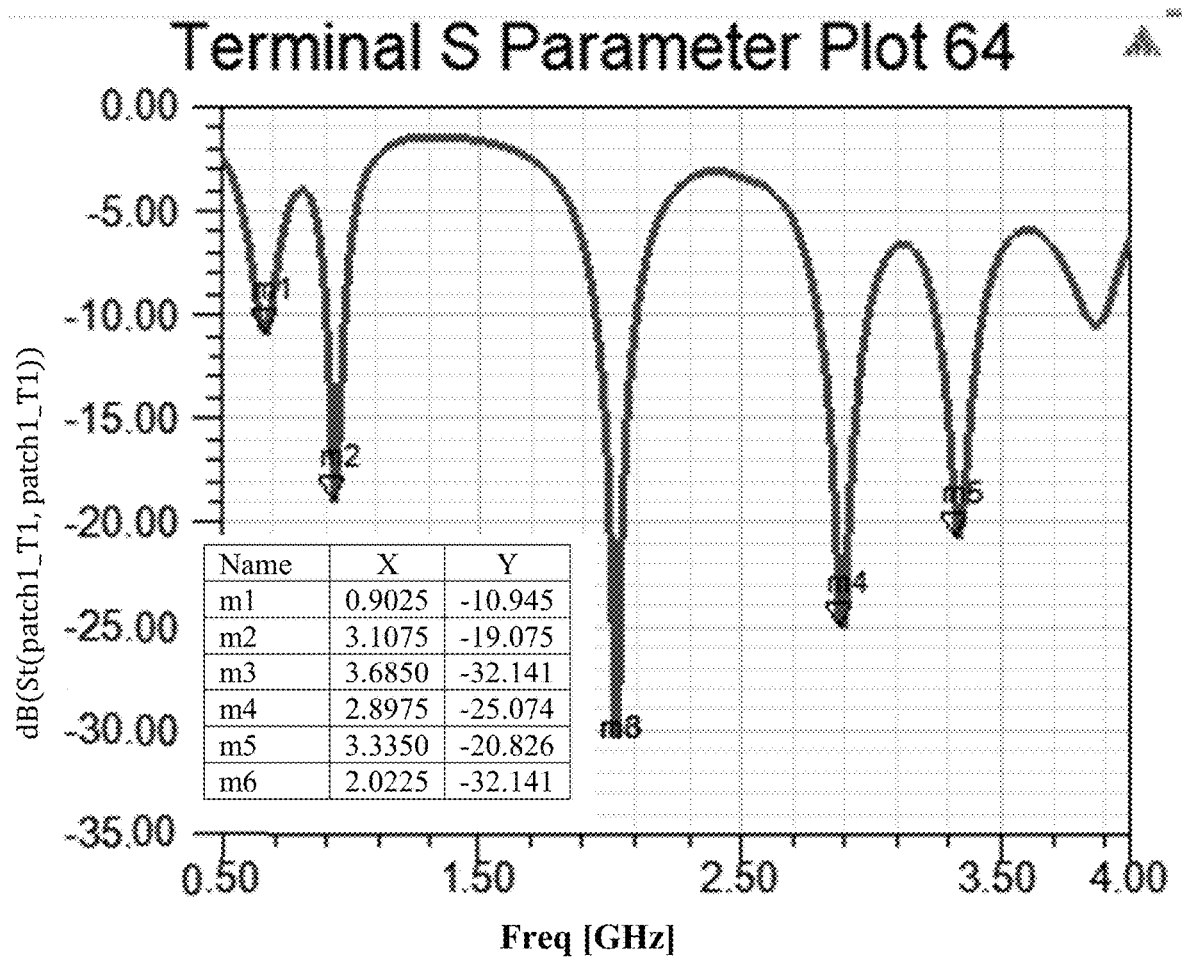
FIG. 7B is a graph of the terminal S parameter plot of FIG. 7A.

As shown in FIG. 7A, in a third embodiment, longer configuration for the length Ls of the sensor array 200. In this embodiment, the sensor array 200 comprises a first slotted sensor 210, a second slotted sensor 220, a third slotted sensor 230, and a fourth slotted sensor 240. The first slotted sensor 210, the second slotted sensor 220, the third slotted sensor 230, and the fourth slotted sensor 240 may be identical, uniform, or heterogeneous. The first slotted sensor 210, the second slotted sensor 220, the third slotted sensor 230, and the fourth slotted sensor 240 may include a slot width of about 1.6 mm. The first slotted sensor 210, the second slotted sensor 220, the third slotted sensor 230, and the fourth slotted sensor 240 include a first slotted arch 110 and a second slotted arch 120 directly connected to the first slotted arch 110 through a top slot 102. The first slotted arch 110 corresponds to the shape of the Peroneal venae comites, and the second slotted arch 120 corresponds to the shape of Posterior tibial venae comites. Further modifications to the first slotted sensor 210, the second slotted sensor 220, the third slotted sensor 230, and the fourth slotted sensor 240 can be obtained from human measurements to define standard sizes for the Peroneal venae comites and the Posterior tibial venae comites. The sensor array 200 as shown in FIG. 7A includes an εr is about 2.33 as shown in FIG. 7B.

Figures 8A, 8B:
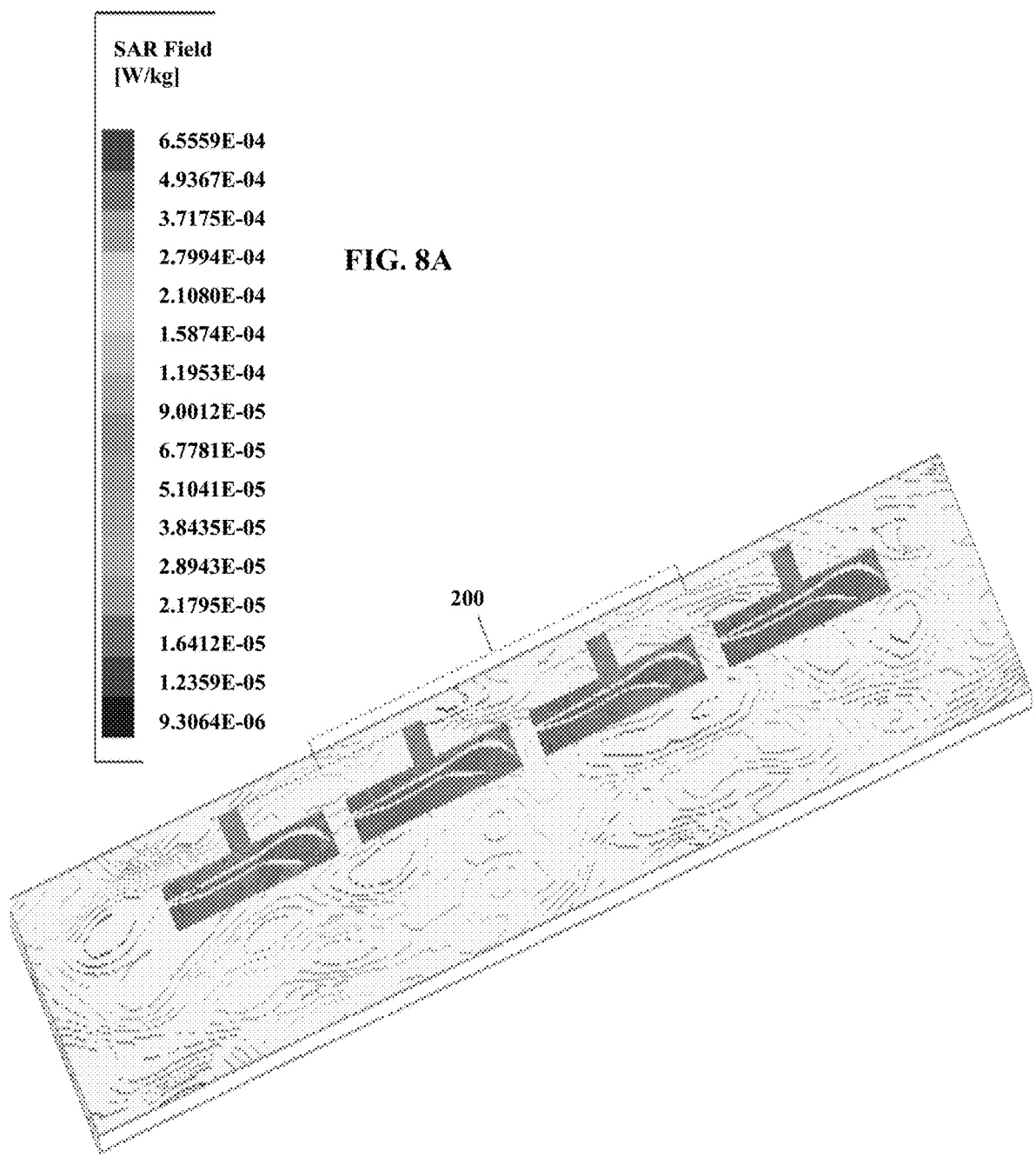
FIG. 8A is a graph of the SAR field showing the values for power=1 W in the sensor array embodiment shown in FIG. 8B.

FIG. 8A shows the values are for power=1 W in the sensor array embodiment shown in FIG. 8B.

Figure 9A:
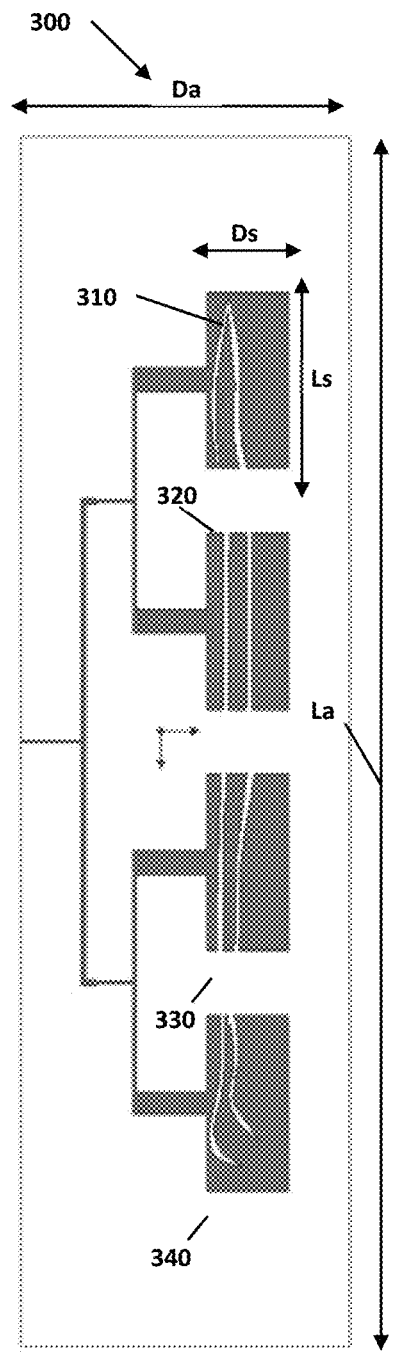
FIG. 9A is a schematic showing the configuration for the sensor array comprising different sensors.
Figure 9B:
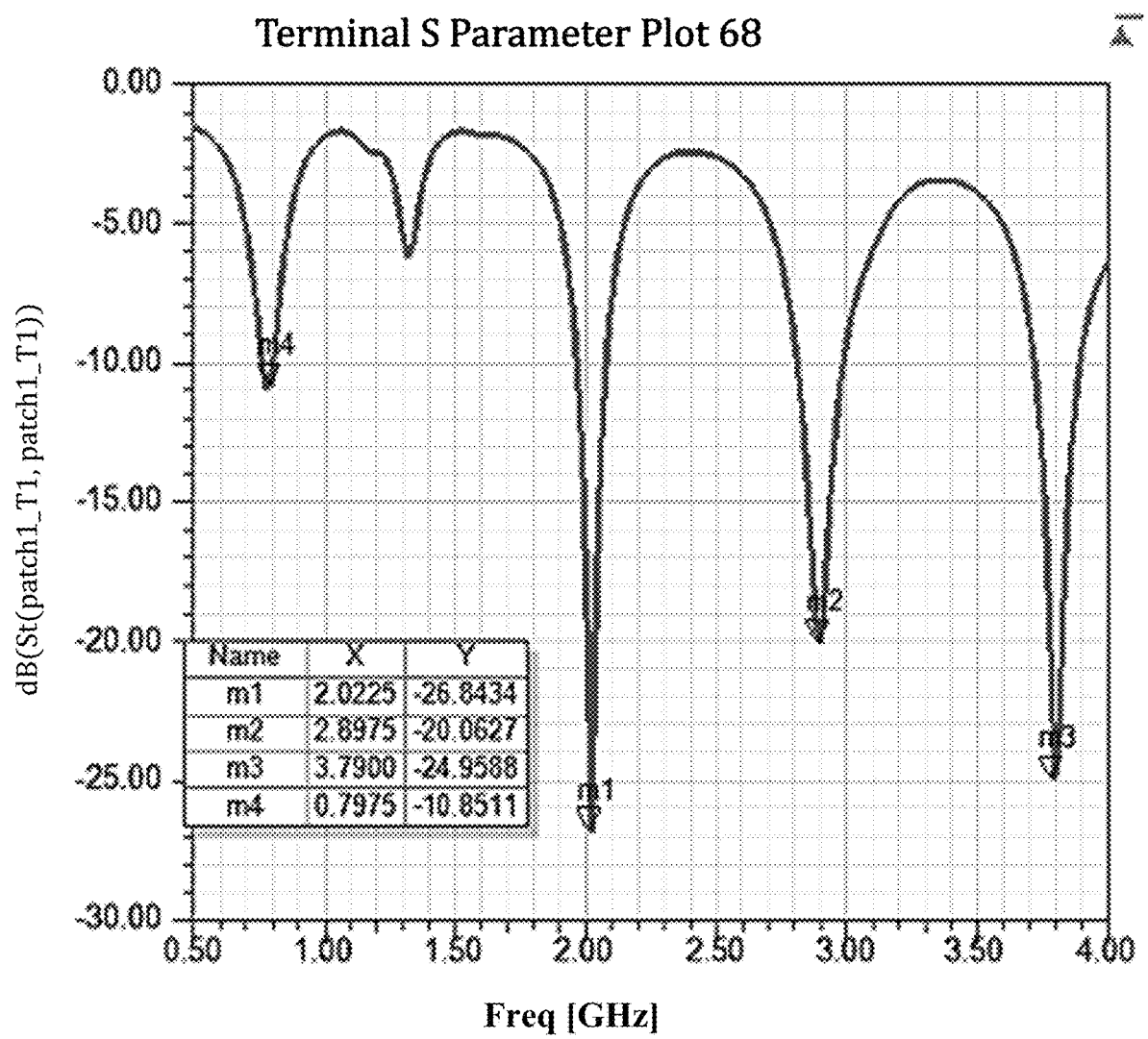
FIG. 9B is a graph of the terminal S parameter plot of FIG. 9A.

As shown in FIG. 9A, in a fourth embodiment, a configuration for the sensor array 300 comprising different sensors. In this embodiment, the sensor array 300 comprises a first slotted sensor 310, a second slotted sensor 320, a third slotted sensor 330, and a fourth slotted sensor 340. The first slotted sensor 310, the second slotted sensor 320, the third slotted sensor 330, and the fourth slotted sensor 340 heterogeneous, where the first slotted sensor 310 includes a substantially V-shape configuration to apply to the top portion of the Peroneal venae comites and posterior venae comites. The second slotted sensor 320 includes a substantially parallel slot configuration to apply to the top middle potion of the Peroneal venae comites and posterior venae comites. The third slotted sensor 330 includes a substantially unparallel slot configuration to apply to the bottom middle potion of the Peroneal venae comites and posterior venae comites. The fourth slotted sensor 340 includes a V-shape curvilinear slot configuration to apply to the bottom potion of the Peroneal venae comites and posterior venae comites. Peroneal venae comites slots include a length Ls: between about 25 mm for the fourth slotted sensor 340 and about 30 mm for the first slotted sensor 310. The Peroneal venae comites slots include a slot width between about 1.0 mm and about 1.5 mm. Posterior tibial venae comites slot include a length Ls about 20 mm for the fourth slotted sensor 340 and about 30 mm for the first slotted sensor 310. The Posterior tibial venae comites slot width between about 1.0 and about 1.5 mm. Further modifications to the first slotted sensor 310, the second slotted sensor 320, the third slotted sensor 330, and the fourth slotted sensor 340 can be obtained from human measurements to define standard sizes for the Peroneal venae comites and the Posterior tibial venae comites. The sensor array 200 as shown in FIG. 9A includes an εr is about 2.33 as shown in FIG. 9B.

Figure 10A:
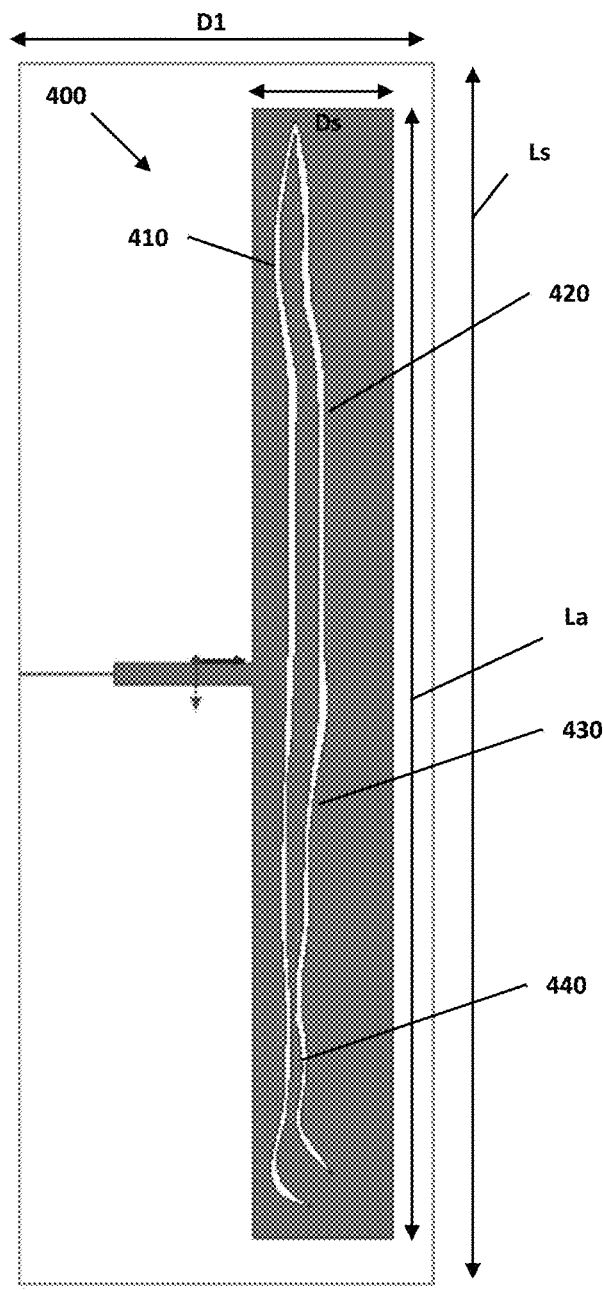
FIG. 10A is a schematic showing the configuration for the sensor comprising different sensor slot sections operably connected on a single substrate and FIG. 10B is a graph of the terminal S parameter plot of FIG. 10A.
Figure 10B:
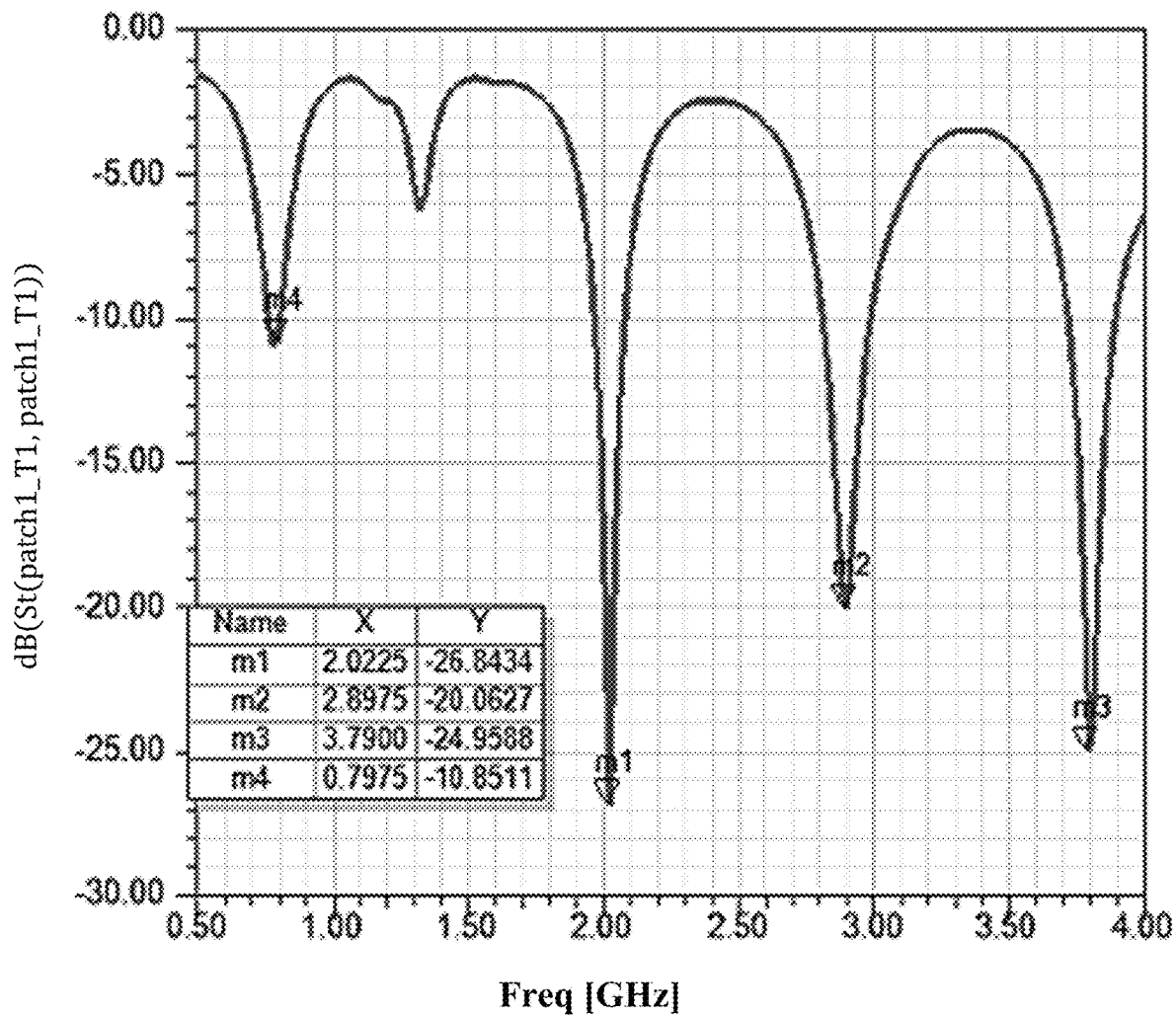

As shown in FIG. 10A, in a fifth embodiment, a configuration for the sensor 400 comprising different sensor slot sections operably connected on a single substrate. In this embodiment, the sensor 400 comprises a first slotted sensor section 410, a second slotted sensor section 420, a third slotted sensor section 430, and a fourth slotted sensor section 440. The first slotted sensor section 410, the second slotted sensor section 420, the third slotted sensor section 430, and the fourth slotted sensor section 440 are heterogeneous, where the first slotted sensor section 410 includes a substantially V-shape configuration to apply to the top portion of the Peroneal venae comites and posterior venae comites. The second slotted sensor section 420 includes a substantially parallel slot configuration to apply to the top middle potion of the Peroneal venae comites and posterior venae comites. The third slotted sensor section 430 includes a substantially unparallel slot configuration to apply to the bottom middle potion of the Peroneal venae comites and posterior venae comites. The fourth slotted sensor section 440 includes a V-shape curvilinear slot configuration to apply to the bottom potion of the Peroneal venae comites and posterior venae comites. Peroneal venae comites slots include a length Ls: between about 140 mm and about 152 mm. The Peroneal venae comites slots include a slot width between about 1.0 mm and about 1.5 mm. Posterior tibial venae comites slot include a length Ls between 140 mm and about 147 mm. The Posterior tibial venae comites slot width between about 1.0 and about 1.5 mm. Further modifications to the first slotted sensor section 410, the second slotted sensor section 420, the third slotted sensor section 430, and the fourth slotted sensor section 440 can be obtained from human measurements to define standard sizes for the Peroneal venae comites and the Posterior tibial venae comites. The sensor 400 as shown in FIG. 10A includes an εr is about 2.33 as shown in FIG. 10B.

For all the embodiments above, the substrate may be a polyethylene terephthalate (PET) with a thickness t=136 um, a Dielectric Constant=2.33, a tangent delta=5.79e-3. The dimensions may include, but are not limited to a Length: 17.3 cm, a Width: 5.6 cm; a Frequency range of interest: 0.5-4 GHz. The sensor embodiments include measured parameters of Reflection coefficients (S11): magnitude and phase.

For all, the above embodiments, when the design topology changes or upon reconfiguration, the antenna performance changes; however, an attached circuit to the device can detect the response at a sweep of different frequency over the pre-defined range of Operation based on the expected stretching distance. The response at the different frequency ranges will then be used to develop a model to predict glucose or constituent levels.

The signal measured from the antenna is converted using a computer program that allow the transformation of the magnitude and the phase of the reflected and/or transmitted signals into concentration of the blood constituents via trained models.

The non-invasive electromagnetic sensor detects the concentration of some blood constituents in human blood stream continuously. The sensor transmits electromagnetic waves into human tissues in order to monitor and detect the variation of the concentration of the blood constituent. The sensor device to convert the detected energy into magnitude and phase.

Figure 11:
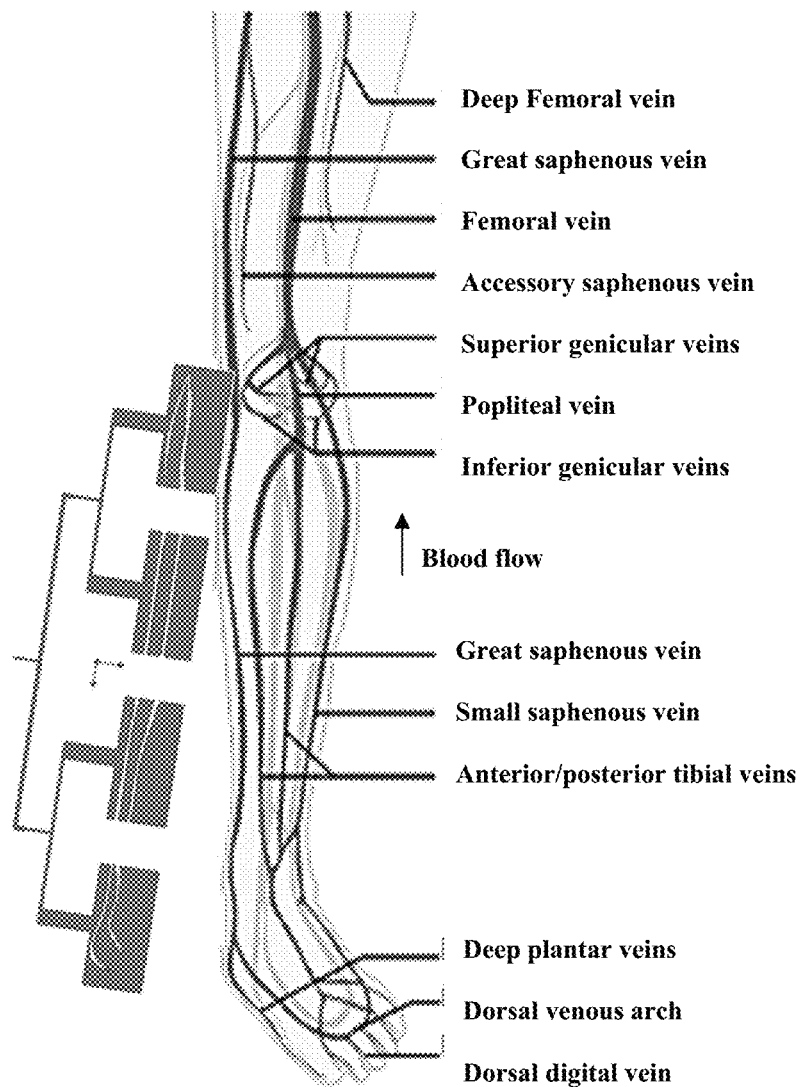
FIG. 11 is a graph showing the measured S11 in when loaded with human model from the sensor of FIG. 9A.

The sensor device processes the detected magnitude and phase and convert it into concentration. The sensor comprises a slot antenna, as shown in FIGS. 1-10. The sensor is operational at multiple frequencies within the frequency band ranging between about 500 MHz and about 1 GHz. The sensor includes the transmission line that is separated from the sensing surface. The sensor is reconfigurable to cover more frequencies within the frequency band ranging from about 500 MHz and about 1 GHz. The sensor includes slots that correspond to the arteries and veins in the human hand, in one embodiment. The sensor includes slots that correspond to the shape of the Peroneal venae comites and the Posterior tibial venae comite, as shown in FIG. 11.

Figure 12:
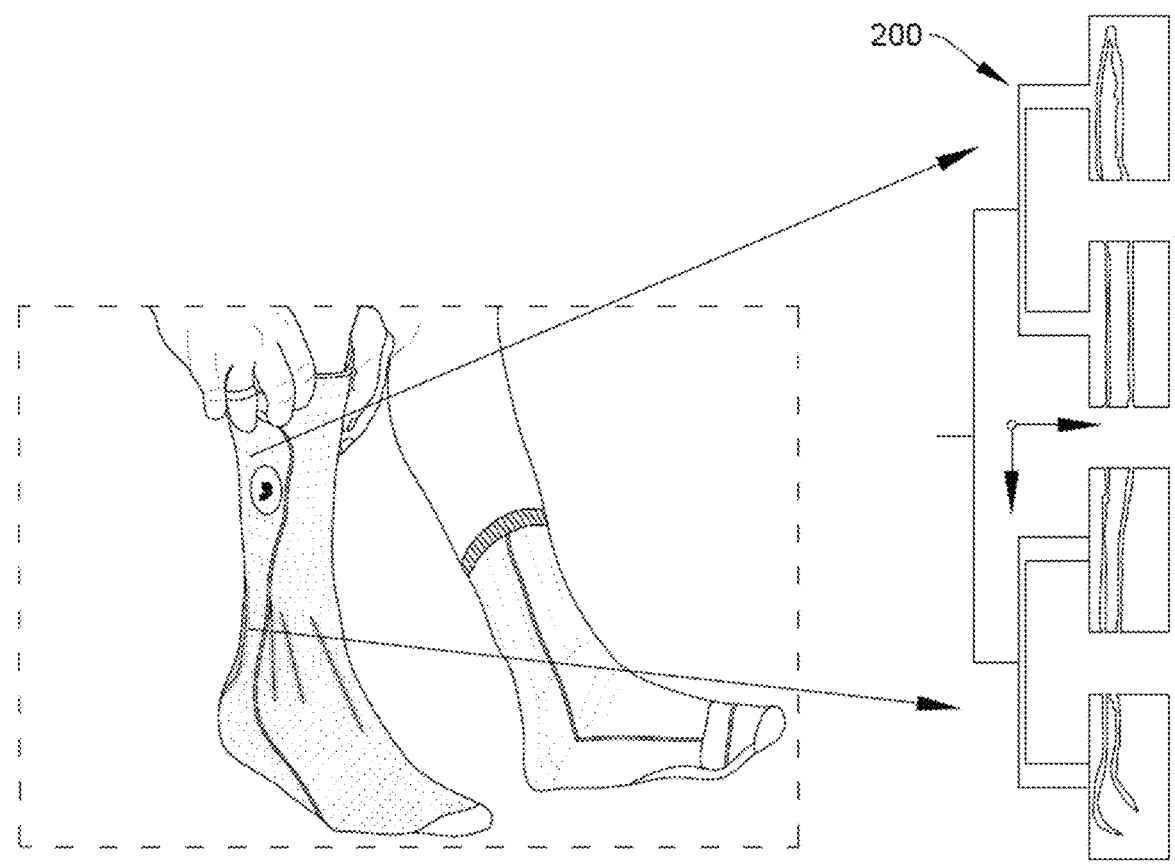
FIG. 12 is a photograph of the sensor embodiment 200 designed using a flexible substrate to be placed easily into a sock, according to one embodiment.

The sensor is designed on dielectric substrate, in one embodiment. The sensor of designed using a flexible substrate to be placed easily into a sock, as shown in FIG. 12. The sensor is connected to a network analyzer to convert the detected energy into magnitude and phase. The sensor is connected to a signal processing system to convert the magnitude and/or the phase into concentration of the blood constituents.

According to one embodiment, this sensor is designed to be operational when loaded with a human leg model. This will make it more sensitive to the variation of the blood constituents levels. The human leg model is composed of 5 layers: a skin layer, fat layer, blood layer, muscle layer and bone layer. Here, the design is to adapt to the topology of the critical area/organ to enhance its sensitivity. The shape of this antenna corresponds to the leg's veins and arteries. The shape of this antenna corresponds to the shape of the Peroneal venae comites and the Posterior tibial venae comite. This distribution increases the sensitivity of the antenna to the variation of the blood constituents levels flowing in the lower leg's veins and arteries. The multiple slots make this antenna operational at multiple frequencies within the UHF frequency and microwave bands ranging between about 500 MHz and about 3 GHz, which provides a practical window to detect the variation of the blood glucose level at different frequencies for different patients.

Feeding methods: In one embodiment, the antenna is fed using a transmission line. Different shapes of transmissions lines could be used to increase the coupling of the slots. For one sensor embodiment, a spiral transmission line as shown in covers as many slots as possible. This makes the antenna operational at lower frequencies within the UHF band and additional resonant frequency appears. (add the simulations for spiral and periodic and simple straight transmission lines) Coaxial feed method could be used to improve the feeding system of the sensor, according to one embodiment.

Other embodiments for the feeding line can be designed to guarantee matching while enabling cross-over between the different slots and feeding line.

Sensor substrate: In one embodiment, the antenna is mounted along with different sensors (humidity, sweat, temperature . . . ) inside an anti-sweat/humidity socks. The sensor is designed on a dielectric substrate with a very thin height. The same sensor can be designed on a flexible substrate to take the shape of each patient's hand. The flexible antenna can also be designed using an adhesive-flexible material such as silicon layers, skin-mounted adhesive and then fixed directly on the patient's hand. "Flexible" is the quality of bending easily without breaking and including a bend radius between about 5 mm and about 1000 mm. flexible plastic substrates, such as polyimide, PEEK, polyester (PET), polyimide (PI), polyethylene naphthalate (PEN), polyetherimide (PEI), along with various fluoropolymers (FEP) and copolymers or transparent conductive polyester film allowing the antennae and sensor to conform to a desired shape, or to flex during its use. An alternative approach to flexible substrates is various etching techniques to thin down the traditional silicon substrate to few tens of micrometers to gain reasonable flexibility, referred to as flexible silicon (~5 mm bending radius).

Adjustment to different Patients: The response of the antenna is expected to change from one patient to another depending on many criteria including but not limited to: Skin thickness, color, type (hairy and glabrous skin); Skin perfusion, hydration; Sweating; Patient metabolism and body mass index; and other medical conditions such as cholesterol, diabetes.

To adjust the response of the antenna, first the linear region is detected using signal processing techniques and then the resonance frequency of the antenna is adjusted to cover this linear zone. The reconfigurable resonance frequency will improve the sensitivity of the sensor and make it more personalized for each patient.

Possible alternate implementations of the design: This sensor can detect the variation of permittivity hence it can be used in different applications such as: Blood Glucose detection and any other blood Biomarkers, hydration monitoring/blood flow, Cholesterol, Bone fracture healing monitoring, cardiac activity: heart rate, blood pressure, and Material/liquid characterization. A similar design can be used to administer localized radiation-based treatment jointly with/without medication to specific underlying patterns/structures.

Metrics that are measured: The sensor is connected to a network analyzer to convert the detected energy into magnitude and phase. For the antenna, S11 parameters are detected including, but not limited to: Magnitude, and Phase or impedance, and to derive the Power level.

Predictive modeling for selection of critical features: The sensor is connected to a signal processing system to convert the magnitude and/or the phase into concentration of the blood constituents. The Predictive modeling for selection of critical features comprises I) Measuring he S11 parameters using the sensor; 2) Preprocessing of the data outlier and noise removal using different techniques (wavelet, moving average filters or other types of filters); 3) extracting feature; 4) Modeling, calibrating and tuning; and 5) recalibrating model for enhanced accuracy.

Preprocessing of the data comprises outlier and noise removal using different techniques (wavelet, moving average filters or other types of filters); Extracting features comprise S11 Magnitude, S11 phase and/or impedance is sampled into different frequency components. The features are then normalized (between −1 and 1): Remove the reference value (equivalent to the values corresponding to a glucose concentration of 80 mg/dl for example); Remove the mean of each metric; Divide by the maximum of each metric.

Modeling, calibrating and tuning comprises regularized regression in one embodiment is used to predict the glucose concentrations (Lasso, PLS, Hybrid models . . . ). Single feature model and multiple-feature models can be used in some embodiments. Time based models can be used.

In one embodiment, the antennae is a Rigid Antennae with the following parameter for the Substrate: Rogers RO3203, Thickness t=0.51 mm, Dielectric fa=3.02; (The thickness and dielectric values may vary to +/−5% due to fabrication methods for this type of substrate.) As such, the Thickness t may be between about 0.45 mm and about 0.54 mm; and the Dielectric fa is between about 2.80 and about 3.20. In one embodiment, the dimensions: 70*70*0.51 mm 3; Feeding: Spiral; Frequency range of interest: about 0.5 GHz-about 3 GHz; Measured parameters: Reflection coefficients (S11): magnitude and phase. The dimensions may range between about 50-100 mm for the width, about 50-100 mm for the length, and about 0.2 mm to 1.0 mm for the thickness. Alternative substrate material can be utilized and requires redesign of the antenna component, according to one embodiment.

The specific substrate RO3203 has 4 different standard thicknesses at (0.25 mm) 0.020" (0.50 mm) 0.030" (0.75 mm) 0.060" (1.52 mm). In other embodiments, the thickness or another substrate from another provider, or same provider but different production number, (maybe with different dielectric constant or material), the antenna component is redesigned accordingly.

In another embodiment, the antennae includes a flexible substrate, including the following parameters, Substrate: PET (polyethylene terephthalate); Thickness t=136 um; Dielectric Constant εr is about 2.99; tangent delta=5.79e−3; (The thickness, dielectric constant, and tangent delta values may vary due to fabrication errors for a specific substrate series.) Substrate providers offer different substrate materials and thickness. Most popular are Kapton® Polymides. https://v-ΛV\v.dupont.com/electronic-materials/kapton-polvimide-film.html As such, for example, for the specific substrate, the Thickness t may be between about 129 μm and about 143 μm; the dielectric constant may also be subject to fabrication process variation; and so does the tangent delta. Dimensions: 70*80*0.5 1 mm$^3$; Feeding: Spiral; Frequency range of interest: is between about 0.5 GHz-3 GHz; Measured parameters: Reflection coefficients (SI 1): magnitude and phase. PET is used in one embodiment as the polymer; other types flexible material exist such as paper substrates [9], and other flexible substrate requires a complete redesign of the entire antenna component. While a wide range of thickness may be incorporated into the embodiments, most flexible films are provided in a narrow range of relatively thin dimension from about 12 μm to about 125 μm (½ mil to 5 mils) as thinner and thicker material are possible in other embodiments. [9] Kim, Sangkil, and Manos M. Tentzeris. "Parylene coated waterproof washable inkjet-printed dual-band antenna on paper substrate." International Journal of microwave and Wireless Technologies 10.7 (2018): 814-818.

Modeling Techniques

The reflection coefficient S11 phase and magnitude measurements obtained for a given antenna (rigid or flexible) at multiple frequencies are used for the estimation of glucose levels, according to one embodiment.

Different regression techniques are tested to best identify the most suitable models that capture the underlying variation in glucose level. Radial basis function (RBF), Gaussian Process (GP), Locally weighted Partial least square (LW_PLS) enable several desired properties, including, but not limited to: sparsity, reduced variance and capture more accurately the local behavior. Particularly, there is a need for localized model coverage to enhance accuracy in the regions corresponding to low glucose level. Other regression techniques include Partial least square (PLS) and Least absolute shrinkage and selection operator (LASSO).

The PLS is a regression technique based on sparsity and maximizing correlations. It generates new regressors, called PLS directions, which are formed by linearly combining the original variables, depending on their univariate influence on the target. Hence the importance of this technique is that it creates the PLS directions by maximizing both their variance of the new regressors (similar to principal components) and the correlation of the regressors with the output variables.

Radial Basis Function (RBF) is a nonlinear regression technique that utilizes basis function (Radial basis function): $y=f(x)=\sum_k w_k b_k(x)$ for the ID case. A radial function is a function that is radially symmetric around some point xc called the function's center. Different RBFs could be used. Optimization methods are utilized to find the best function centers and parameters.

Gaussian process (GP) is a modeling technique that also provides uncertainty information about the estimate at a given point xq. This technique relates the point xq to the different training points x using a covariance function, k(x, xq) based on their distance, so again it can emphasize the local influence of the training points depending on the model parameters.

In Locally weighted PLS, PLS is used to build a local linear regression model specific for each new point, x0, whose performance is to be predicted. The model provides distance based weights for each training point, based on the distance between x0 and the different training points. The process is iterative and the model underneath uses linear regression in the form of PLS (unlike RBF and GP). So it employs PLS directions as new regressors.

For each x0, the newly generated local model strongly depends on the similarity/proximity between x0 and the training samples. In the model, the Euclidean distance was distance.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C., or is at ambient temperature, and pressure is at or near atmospheric.

Example 1: In Vitro Experiment on Serum

Experimental Setup for the in vitro experiment includes a foam container is filled with 30 ml of Fetal Bovine Serum PBS/glucose solutions, which is very close to the blood in terms of composition. Foam dimension: same size of the antenna (70*70 mm$^2$ and a thickness of 0.5 cm.

The container is kept fixed during the whole experiment.

An initial measurement is done. A reference glucose level is taken using the Glucotrack glucometer from Roche. For each measurement, 10 repeated readings for the S11 magnitude and phase are taken using the vector network analyzer (VNA). This is to average out any error resulting from the measurements. The S11 values were recorded over the whole desired frequency range.

After each measurement, the glucose level was increased slightly for the next measurements. A small amount of glucose, equivalent to 10 mg/dl, is added to the FBS solutions. After each addition of glucose, the FBS solution is mixed and left for 10 minutes to insure the homogeneity of the solution. The same procedure is repeated until the glucose levels of the FBS reaches around 500 mg/dl. Same experiment is done on both the rigid and flexible antennas: A total of 41 measurements were taken for the rigid antenna and 38 measurements for the flexible one.

Individual OGTT models were developed. Normalization performed within each OGTT. 10 random replications (division in test and train data) were performed for each OGTT to give better idea about the error. Only GP (Gaussian process) was adopted. Glucose concentration of the FBS solution was varied with very small steps from 50 mg/dl to 445 mg/dl. The normalized S11 versus the reference glucose levels obtained by the commercial invasive glucometer.

Example 2: Sensitivity Test

A vessel like container made of foam is filled with 14 ml of FBS. Two experiments were conducted to prove the importance of concentrating the EM waves on the veins. An initial measurement is done. A reference glucose level is taken using the Glucotrack glucometer from Roche. 10 savings for the S11 magnitude and phase are taken using the VNA. After each measurement a small amount of glucose, equivalent to 100 mg/dl, is added to the FBS solutions.

After each addition of glucose, the FBS solution is mixed and left for 10 minutes to insure the homogeneity of the solution. The same procedure is repeated until the glucose levels of the FBS reaches around 500 mg/dl. This experiment is done using the rigid antenna: A total of 7 data points were collected in both experiments Example 3: Ex-Vivo Experiment on Rat Skin Fresh abdominal rat skin is dissected and cut into a 70 by 70 mm and preserved in Phosphate-buffered saline (PBS) solution. The skin with the PBS is paced in a foam container. Foam dimension: same size of the antenna (70*70 mm) and a thickness of 0.5 cm. The container is kept fixed during the whole experiment. A thin nylon container is filled with 14 ml of Fatal Bovine Serum PBS/glucose solutions which is very close to the blood in terms of composition. An initial measurement is done and a reference glucose level is taken using the Glucotrack glucometer from Roche. 10 savings for the S11 magnitude and phase are taken using the VNA.

After each measurement a small amount of glucose, equivalent to 100 mg/dl, is added to the FBS solutions. After each addition of glucose, the FBS solution is mixed and left for 10 minutes to insure the homogeneity of the solution. The same procedure is repeated until the glucose levels of the FBS reaches around 500 mg/dl. Same experiment is done on both antennas: A total of measurements of 14 were taken for the rigid antenna and from the flexible one.

Example 3: In Vivo Experiment on Rats

Rat species: Sprague Dawley rats The animals were housed in the Animal Care Facility of the American University of Beirut, in rack-mounted wire cages, with a maximum of 5 rats per cage and kept on a 12 hours light/dark cycle in a controlled temperature and humidity room. Standard laboratory pelleted formula and tap water were provided ad libitum. The experiment was carried out in accordance to the guidelines of the Institutional Animal Care and Use Committee (IACUC) at the American University of Beirut" [1] [1] Gerges, Alice & Rizzo, M & Eid, Assaad & Hajj Hussein, Inaya & Zgheib, Z & N Zeenny, M & Jujus, Rosalyn & Uzzo, Maria & Spatola, Giovanni & Bonaventura, Giuseppe & Leone, Angelo & Massaad-Massade, Liliane & Jujus, Abdo. (2017). Tea catechins induce crosstalk between signaling pathways and stabilize mast cells in ulcerative colitis. Journal of biological regulators and homeostatic agents. 31. 865-877.

The animal weighed around 700 g. A rat is studied after 8-hour overnight fast. Thirty minutes prior to the testing, the rat is anesthetized using inhaled anesthetic, Forane. The rat is anesthetized just during the fixation of the antenna on his back, whereas during the experiment the rat is awake. The measurement area of the hairy mice is shaved prior to the placement of the antenna to avoid the influence of possible external factors on the measurements. The antenna is fixed on the back of the rat with a foam separation of 0.5 cm and connected to the portable VNA. The animal is than placed in a restrainer in order to limit his movement during the experiment An Intraperitoneal injection glucose tolerance test (IP-GTT) is conducted. At time 0, the rat receives an intraperitoneal injection of 0.2 ml of saturated glucose solution. Measurements using both the VNA and a glucometer are done every 5 minutes. A reference glucose level using invasive glucometer, and for each measurement, 10 repeated readings for the S11 magnitude and phase are taken using the VNA. This is to average out any error resulting from the measurements. The S11 values were recorded over the whole desired frequency range.

Example 3: In Vivo Experiment on Human Subjects

Before each visit, the subjects are asked not to eat or drink anything 8 hours before coming to the clinic.
1. Fixation of the sensing system: The subjects are asked to sit on a chair to limit the body movements. The rigid and the flexible antennas are placed on both hands and measurements will be taken simultaneously from both antennas. The antennas are fixed on the hands using Gauze Wrap and connected to a portable VNA. The antenna is not in contact directly on your skin, it will be separated by a 0.5 cm of foam.
2. Fasting glucose blood test: after the fixation of the sensing system, a first reference measurement is taken using an invasive glucometer and 10 savings from the VNA simultaneously.
3. Glucose intake: The subjects are asked to consume 75 grams of sugars by eating 500 ml of ice-cream in 10-15 minutes Glucose test: the same procedure described in step 3 (Fasting glucose blood test) is repeated every 15 minutes for two hours. VNA savings are taken every 5 minutes. The oral glucose tolerance test takes about 2 hours to be completed. Each subject repeats this procedure for a total of 3 times, on 3 different days. The data for a group of healthy individuals aging between 25 to 60 years old to take part is presented. All the participants are from a healthy controlled group.
[0117] Example: Detection of Different Glucose Levels The free space multi-band characteristic, enables the analysis of the antenna's response at different frequencies thereby allowing for a more holistic contactless characterization of blood constituents with improved sensitivity. A foam container filled with FBS glucose solution is placed above the sensing layer of the slot antenna. The antenna is connected to a vector network analyzer (VNA) to measure its S11 coefficient over the 0.5-1.5 GHz frequency span. The antenna is fixed during the whole experiment, and the glucose concentration of the FBS solution is varied with a step of 50 mg/dl to cover a wide range of concentrations representing a glycemic range that varies from 28 to 471 mg/dl. The actual glucose levels are measured using an invasive-glucometer (Accu-Chek from ROCHER). When the antenna is loaded with the FBS solution, a clear shift in its S11 magnitude is noticed.

System

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Software includes applications and algorithms. Software may be implemented in a smart phone, tablet, or personal computer, in the cloud, on a wearable device, or other computing or processing device. Software may include logs, journals, tables, games, recordings, communications, SMS messages, Web sites, charts, interactive tools, social networks, VOIP (Voice Over Internet Protocol), e-mails, and videos.

In some embodiments, some or all of the functions or process(es) described herein and performed by a computer program that is formed from computer readable program code and that is embodied in a computer readable medium. The phrase "computer readable program code" includes any type of computer code, including source code, object code, executable code, firmware, software, etc. The phrase "computer readable medium" includes any type of medium capable of being accessed by a computer, such as read only memory (ROM), random access memory (RAM), a hard disk drive, a compact disc (CD), a digital video disc (DVD), or any other type of memory.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A sensor to non-invasively detect the concentration of biomarkers comprising: an antenna array including a plurality of sensors that are configured to track the topology of the arteries and veins, or nerves in a specific location of the human body; wherein each sensor comprises a first slotted arch and a second slotted arch; the first slotted arch and the second slotted arch are directly connected through a top slot; wherein the first slotted arch corresponds to the shape of the Peroneal venae comites, and the second slotted arch corresponds to the shape of Posterior tibial venae comites; the first slotted arch includes a long slotted main branch connected to a distal curvilinear branch; the long slotted main branch connects to the top slot, wherein the top slot is a substantially V-shape; the second slotted arch includes a second long main branch that correspond to the Posterior tibial venae comites or the anterior tibial venae comites; the second long main branch includes a second distal curved branch; and a feeding transmission line configured to transmit electromagnetic waves into human tissues in areas in close proximity to the arteries and veins or nerves, wherein each sensor is configured to monitor and detect responses proportional to the concentration of the blood constituents.

2. The sensor of claim 1, wherein the distal curvilinear branch includes an angle of curvature between about 55 degrees and about 120 degrees.

3. The sensor of claim 2, wherein the first slotted arch is the Peroneal venae comites slot including a length of about 25 mm and a slot width between about 0.5 mm and about 1 mm.

4. The sensor of claim 3, wherein the second slotted branch is the Posterior tibial venae comites slot including a length of about 21 mm and a slot width between about 0.5 mm and about 1 mm.

5. The sensor of claim 4, wherein the antenna array includes a dielectric constant $\varepsilon_r$ about 2.99.

6. The sensor of claim 1, wherein each sensor corresponding to a sensor diameter Ds is in range of about 10.0 mm to about 17.0 mm and a sensor length Ls between about 25.0 mm to about 35 mm for proper coverage of the veins.

7. The sensor of claim 6, wherein the antenna array include an array diameter Da is in the range of about 45.0 mm to about 65.0 mm, and an array length La in the range of about 155 mm to about 190 mm.

8. The sensor of claim 1, wherein the plurality of sensors comprises a first slotted sensor, a second slotted sensor, a third slotted sensor, and a fourth slotted sensor; the first slotted sensor, the second slotted sensor, the third slotted sensor, and the fourth slotted sensor and each include a slot width of about 1.6 mm; the first slotted sensor, the second slotted sensor, the third slotted sensor, and the fourth slotted sensor each include a first slotted arch and a second slotted arch directly connected to the first slotted arch through a top slot; the first slotted arch corresponds to the shape of the Peroneal venae comites, and the second slotted arch corresponds to the shape of Posterior tibial venae comites.

9. The sensor of claim 8, wherein the antenna array includes a dielectric constant εr about 2.99.

10. The sensor of claim 1, wherein the feeding transmission line comprising a spirally shaped feeding transmission line with three turns in a spiral configuration that are positioned on the bottom layer of the antenna array such that the transmission line is separated from the sensing surface; wherein the antenna resonates when it is loaded with a typical human leg tissue to increase its sensitivity to the variation of the blood constituents.

11. The sensor of claim 10, wherein the antenna array is operational above or below UHF, L-bands and lower S-bands ranging between about 500 MHz and about 3 GHz.

12. The sensor of claim 11, wherein the antenna array includes a stretching property limited to be 10% over the width and the length of the slot, wherein the stretched antenna array maintains resonance levels below −10 db.

13. The sensor of claim 12, wherein the substrate is a polyethylene terephthalate (PET) with a thickness t=136 um, a Dielectric Constant=2.33, a tangent delta=5.79e−3.

14. A sensor array comprising a first slotted sensor, a second slotted sensor, a third slotted sensor, and a fourth slotted sensor operably coupled on a substrate; wherein the first slotted sensor, the second slotted sensor, the third slotted sensor, and the fourth slotted sensor are heterogeneous; wherein the first slotted sensor includes a substantially V-shape configuration to apply to the top portion of the Peroneal venae comites and posterior venae comites; the second slotted sensor includes a substantially parallel slot configuration to apply to the top middle potion of the Peroneal venae comites and posterior venae comites; the third slotted sensor includes a substantially unparallel slot configuration to apply to the bottom middle potion of the Peroneal venae comites and posterior venae comites; the fourth slotted sensor includes a V-shape curvilinear slot configuration to apply to the bottom potion of the Peroneal venae comites and posterior venae comites; the peroneal venae comites slots include a length Ls between about 25 mm for the fourth slotted sensor and about 30 mm for the first slotted sensor; the Peroneal venae comites slots include a slot width between about 1 mm and about 1.5 mm; the Posterior tibial venae comites slot include a length Ls about 20 mm for the fourth slotted sensor and about 30 mm for the first slotted sensor; the Posterior tibial venae comites slot width between about 1.0 and about 1.5 mm.

15. The sensor array of claim 14, further comprising a dielectric constant εr about 2.33.

16. A sensor comprising: different sensor slot sections operably connected on a single substrate; wherein the different sensor slot sections include a first slotted sensor section, a second slotted sensor section, a third slotted sensor section, and a fourth slotted sensor section; the first slotted sensor section, the second slotted sensor section, the third slotted sensor section, and the fourth slotted sensor section are heterogeneous; wherein the first slotted sensor section includes a substantially V-shape configuration to apply to the top portion of the Peroneal venae comites and posterior venae comites; the second slotted sensor section includes a substantially parallel slot configuration to apply to the top middle potion of the Peroneal venae comites and posterior venae comites; the third slotted sensor section includes a substantially unparallel slot configuration to apply to the bottom middle potion of the Peroneal venae comites and posterior venae comites; the fourth slotted sensor section includes a V-shape curvilinear slot configuration to apply to the bottom potion of the Peroneal venae comites and posterior venae comites; the Peroneal venae comites slots include a length Ls between about 140 mm and about 152 mm; the Peroneal venae comites slots include a slot width between about 1.0 mm and about 1.5 mm; the Posterior tibial venae comites slot includes a length Ls between 140 mm and about 147 mm; the Posterior tibial venae comites slot width is between about 1.0 and about 1.5 mm.

17. The sensor of claim 16, further comprising a dielectric constant εr about 2.33.

18. The sensor of claim 17, wherein the substrate is a polyethylene terephthalate (PET) with a thickness t=136 um, a Dielectric Constant=2.33, a tangent delta=5.79e-3; the sensor responsive to a Frequency range of interest between about 0.5-4 GHz and configured to measure parameters of Reflection coefficients (S11): magnitude and phase.

19. The sensor of claim 18, wherein the signal measured from the sensor is converted using a computer that transforms the magnitude and the phase into concentration of the blood constituents via trained models.

* * * * *